United States Patent [19]
Chang et al.

[11] Patent Number: 5,834,283
[45] Date of Patent: Nov. 10, 1998

[54] ACYL COENZYME A:CHOLESTEROL ACYLTRANSFERASE (ACAT)

[75] Inventors: Ta-Yuan Chang; Catherine C. Y. Chang, both of Hanover, N.H.

[73] Assignee: Trustees of Dartmouth College, Hanover, N.H.

[21] Appl. No.: 509,187

[22] Filed: Jul. 31, 1995

Related U.S. Application Data

[60] Division of Ser. No. 121,057, Sep. 10, 1993, Pat. No. 5,484,727, which is a continuation-in-part of Ser. No. 959,950, Oct. 14, 1992, abandoned.

[51] Int. Cl.$^6$ ............................ C12N 9/10; C07M 21/04
[52] U.S. Cl. ......................................... 435/493; 536/23.2
[58] Field of Search ............................ 435/193; 536/23.2

[56] References Cited

U.S. PATENT DOCUMENTS

| | | | |
|---|---|---|---|
| 4,652,639 | 3/1987 | Stabinsky | 336/23.1 |
| 5,023,243 | 6/1991 | Tullis | 514/44 |
| 5,075,227 | 12/1991 | Hagen | 435/172.3 |
| 5,173,408 | 12/1992 | Large, III et al. | 435/198 |
| 5,215,915 | 6/1993 | Tiberi et al. | 435/252.3 |
| 5,217,865 | 6/1993 | Myerowitz | 435/6 |
| 5,281,520 | 1/1994 | O'Hara et al. | 435/69.1 |

FOREIGN PATENT DOCUMENTS

| | | |
|---|---|---|
| WO 91/07483 | 5/1991 | WIPO . |
| WO 93/06123 | 4/1993 | WIPO . |
| WO 93/07280 | 4/1993 | WIPO . |

OTHER PUBLICATIONS

Babbitt et al., (1992) "Ancestry of the 4–Chlorobenzoate Dehalogenase: Analysis of Amino Acid Sequence Identities among Families of Acyl: Adenyl Ligases, Enoyl–CoA Hydratases/Isomerases, and Acyl–CoA Thioesterases," *Biochemistry*, vol. 31, 5594–5604.

Cadigan et al., (1988) "Isolation and Characterization of Chinese Hamster Ovary Cell Mutants Deficient in Acyl–Coenzyme A: Cholesterol Acyltransferase Activity, " *Journal of Biological Chemistry*, vol. 263(1), 274–282.

Cadigan, K.M., et al., (1989), "Isolation of Chinese Hamster Ovary Cell Lines Expressing Human Acyl–Coenzyme A/Cholesterol Acyltransferase Activity," *The Journal of Cell Biology*, vol. 108, No. 6, 2201–2210.

Cadigan et al., (1988) "A simple method for reconstitution of CHO cell and human fibroblast acyl coenzyme A: cholesterol acyltransferase activity into liposomes" *Journal of Lipid Research*, vol. 29(12), 1683–1692.

Cadigan et al., (1990) "Isolation and Characterization of Chinese Hamster Ovary Cell Mutants Defective in Intracellular Low Density Lipoprotein–Cholesterol Trafficking" *The Journal of Cell Biology*, vol. 110(2), 295–308.

Chang and Doolittle, (1983) "Acyl Coenzyme A:Cholesterol O–Acyltransferase," *The Enzymes*, vol. 16, 523–539.

Chang, C. and T.Y. Chang (1993) "Molecular Cloning and Functional Expression of Human Acyl–Coenzyme A:Cholesterol Acyltransferase (ACAT) cDNA", *The FASEB Journal*, vol. 7, No. 7, A1147, Abstract No. 551.

Chang et al., (1993), "Molecular Cloning and Functional Expression of Human Acyl–Coenzyme A:Cholesterol Acyltransferase cDNA in Mutant Chinese Hamster Ovary Cells", *The Journal of Biological Chemistry*, vol. 268, No. 28, 20747–20755.

Chauton et al., (1988) "Acyl–Coenyzme A:Cholesterol Acyltransferase Assay: Silica Gel Column Separation of Reaction Products" *Analytical Biochemistry*, vol. 173(2), 436–439.

Doolittle, (1981) Dissertation Abstracts International, vol. 24(4), 1429B.

FortKamp et al., (1986) "Cloning and Expression in *Escherichia coli* of a Synthetic DNA for Hirudin, the Blood Coagulation Inhibitor in the Leech" *DNA*, vol. 5(6), 511–517.

International Search Report issued during prosecution of PCT/US 93/09704, received May 26, 1994.

Jolly et al., (1982) "Isolation of a genomic clone partially encoding human hypoxanthine phosphoribosyltransferase," *Proceedings of the National Academy of Sciences*, vol. 79, 5038–5041.

Kinnunen et al., (1988) "Chemical Modification of Acyl–CoA:Cholesterol O–Acyltransferase. 1.) Idenitification of Acyl–CoA:Cholesterol O–Acyltransferase Subtypes by Differential Diethyl Pyrocarbonate Sensitivity," *Biochemistry*, vol. 27, No. 19, 7344–7350.

Little et al., (1992) "Ontogeny of acyl–CoA: cholesterol acyltransferase in rat liver, intestine, and adipose tissue" *American Journal of Physiology*, vol. 262(4), G599–G602.

Metheral et al., (1991) "A 25–Hydroxycholesterol–resistant Cell Line Deficient in Acyl–CoA: Cholesterol Acyltransferase," *Journal of Biological Chemistry*, vol. 266(19), 12734–12740.

O'Brien et al., (1992) "ACAT Inhibitors: A Potential New Approach to the Treatment of Hypercholesterolaemia and Atherosclerosis," *Cardiovasculars*, 507–526.

Schlid et al., (1990) "Cloning of three human multifunctional de novo purine biosynthetic genes by functional complementation of yeast mutations" *Proceedings of the National Academy of Sciences U.S.A.*, vol. 87(8), 2916–2920.

(List continued on next page.)

*Primary Examiner*—Eric Grimes
*Assistant Examiner*—Elizabeth Slobodyansky
*Attorney, Agent, or Firm*—Lahive & Cockfield, LLP

[57] ABSTRACT

This invention pertains to purified, biologically active acyl coenzyme A: cholesterol acyltransferase (ACAT) and to nucleic acid (DNA or RNA) encoding acyl coenzyme A:cholesterol acyltransferase. The nucleic acid, or a fragment thereof, may be ligated with an expression vector and transfected into cells to express acyl coenzyme A:cholesterol acyltransferase activity in intact cells and in cell-free extracts.

5 Claims, 10 Drawing Sheets

OTHER PUBLICATIONS

Spector et al., (1979) "Role of AcylCoenzyme A:Cholesterol O–acyltransferase in Cholesterol Metabolism," *Progress in Lipids Research*, vol. 18, No. 1, 31–53.

Schmitz et al. (1990) Biotechnology of Dyslipoproteinemias: Applications in Diagnosis and Control, C. Lenfant et al. (eds.) Raven Press, New York, pp. 79–89.

Young et al. (1983) Proc. Natl. Acad. Sci. USA 80, pp. 1194–1198.

Sturley ((1997) Current opinion in lipidology 8, pp. 167–173.

Diczfalusy et al. (1996) Arteriosclerosis, thrombosis and vascular biology 16, pp. 606–610.

FIG. 3 gaaaccctgcaaaggagtccctagagacacctagtaatggtcgaattgacataaaacagt
tgatagcaaagaagataaagttgacagcagaggcagaggaattgaagccattttttatga
aggaagttggcagtcactttgatgattttgtgaccaatctcattgaaaagtcagcatcat
tagataatggtgggtgcgctctcacaaccttttctgttcttgaaggagagaaaaacaacc
atagagcgaaggatttgagagcacctccagaacaaggaaagatttttattgcaaggcgct
ctctcttagatgaactgcttgaagtggaccacatcagaacaatatatcacatgtttattg
ccctcctcattctctttatcctcagcacacttgtagtagattacattgatgaaggaaggct
ggtgcttgcaagttacgcctcctgtcttatgcatttggcaaatttcctaccgttgtttg
gacctggtggatcatgttcctgtctacattttcagttccctattttctgtttcaacattg
gcgcactggctatagcaagagttctcatccgctgatccgttctctcttccatggctttct
tttcatgatcttccagattggagttctaggttttggaccaacatatgttgtgttagcata
tcctgccaccagcttcccggttcatcattattcgagcagatcgttttgtaatgaaggccc
actcatttgtcagagagaacgtgcctcgggtactaattcagctaaggagaaatcaagcac
tgttccaatacctacagtcaaccagtatttgtacttcttatttgctcctacccttatcta
ccgtgacagctatcccaggaatcccactgtaagatggggttatgttgctatgaagtttgc
acaggtctttggttgcttttctatgtgtactacatctttgaaaggctttgtcccccctt
gtttcggaatatcaaacaggagcccttcagcgctc

FIG. 6A

```
gggtagagacggggtttcaccgtgttagccaggatggtctggatctcctgacctcgtgatccac
ccacctcggcctcctaaagtgctgggattacagacatgagccaccgcgcccagccctattcatc
ccttttcaaaagtcagaccctaggaagctggagggaggtggggcatggttttacagtgaatttc
tgatttcactcaggtgataaatcagactcttggggaagcgggtggtggctctggacagcagca
ggaatggggatccagttagcaacaaatccatggacctatgacaggctgaaagccaccccttctc
catctttggaggttgccaatgtctgatttaacactatccaatgaatgatcattgaaagtaaaa
aataactatcaactagcagaaatataaatggtaagcattagcacatatttcacatgtttatat
ttggctctcagattgacctataaaacaaagtctgggaaattctatatgatcctgaaaaatgat
acgctggtctggatggtagaataagttggagaaatgtttaagccaaaatgcagtcttaccaatg
acttttatttattttattaattttcaggattttggtatacaggtggttttggttacatgg
aaaagttctttactggtgatttctgagattttagttcaccccttatcctgagcagtgtacactg
ttcccaatatgtagcctttatccctcacccctctaagttcaagaagactatggtcctgcaga
aagctttatatgtaattaacatatctttatctttatctttataggcagtagactcatcttttga
aacagattccattaagagtgaatgtgtaccctcctctagcctttattattactgttttgcta
ttacatgtgttagtgtatgtgaatttaatgcttaaaaatgtatcccattggctactatggcaaa
aggttgactcataagagtttagcacgggttaagatctgaaagttttctNNcccagcctcttatc
actggcNagacttcacaattcatggaagccaccagtgagatgacattagcacgggtagtcgatt
tgcagcctcttatcactgNNNNagacttcacaattcatggaacaggaatgacatttcgctcagg
cagttactgtttttatattctataactcgaggagctcagggctttcggaaatcattaaactttc
cttgtccttttaaagttggagccagcaattgtagacagccttccagtgggttatcttttgtgt
ctccttacctgtggagaagcctattagctggatatattattaaatagctatatttatatatc
cagggcacccgaattcggggagagcttcccggagtcgaccttcctgctggctgctctgtgacgct
tcccgctctgcctcttggccgaagtcgcgctgccgggcgcgggcctcagacaatacaatggtg
ggtgaagagaagatgtctctaagaaaccggctgtcaaagtccagggaaaatcctgaggaagatg
aagaccaggagaaaccctgcaaaggagtccctagagacacctagtaatggtcgaattgacataa
aacagttgatagcaaagaagataaagttgacagcagaggcagaggaattgaagccattttttat
gaaggaagttggcagtcactttgatgatttgtgaccaatctcattgaaaagtcagcatcatta
gataatggtgggtgcgctctcacaaccttttctgttcttgaaggagagaaaaacaaccatagag
cgaaggatttgagagcacctccagaacaaggaaagatttttattgcaaggcgctctctcttaga
tgaactgcttgaagtggaccacatcagaacaatatatcacatgtttattgccctcctcattctc
tttatcctcagcacacttgtagtagattacattgatgaaggaaggctggtgcttgcaagttacg
cctcctgtcttatgcatttggcaaatttcctaccgttgtttggacctggtggatcatgttcct
gtctacattttcagttccctatttctgtttcaacattggcgcactggctatagcaagagttct
catccgctgatccgttctctcttccatggctttcttttcatgatcttccagattggagttctag
gttttggaccaacatatgttgtgtagcatatcctgccaccagcttccggttcatcattattc
gagcagatcgtttgtaatgaaggcccactcatttgtcagagagaacgtgcctcgggtactaat
tcagctaaggagaaatcaagcactgttccaataccctacagtcaaccagtatttgtacttcttat
ttgctcctacccttatctaccgtgacagctatcccaggaatcccactgtaagatgggttatgt
tgctatgaagtttgcacaggtctttggttgcttttctatgtgtactacatctttgaaaggctt
tgtgccccttgtttcggaatatcaaacaggagcccttcagcgctcgtgttctggtcctatgtg
```

FIG. 6B

```
tatttaactccatcttgccaggtgtgctgattctcttccttactttttttgccttttttgcactg
ctggctcaatgcctttgctgagatgttacgctttggtgacaggatgttctataaggattggtgg
aactccacgtcatactccaactattatagaacctggaatgtggtggtccatgactggctatatt
actatgcttacaaggactttctctggttttctccaagagattcaaatctgctgccatgttagc
tgtctttgctgtatctgctgtagtacacgaatatgccttggctgtttgcttgagcttttctat
cccgtgctgttcgtgctcttcatgttctttggaatggctttcaacttcattgtcaatgatagtc
ggaaaaagccgatttggaatgttctgatgtggacttctcttttcttgggcaatggagtcttact
ctgcttttattctcaagaatggtatgcacgtcggcactgtacctctgaaaaatcccacattttt
ggattatgtcctgtcacgttcctggacttgtcgttacgtgttttagaagcttggactttgtttc
ctccttgtcactgaagattgggtagctccctgatttggagccagctgtttccagttgttactga
agttatctgtgttatttggaccactccaggctttacagatgactcactccattcctaggtcact
tgaagccaaactgttggaagttcactggagtcttgtacacttaagcagaggagaactttttttg
tggggctgggtggggggagaagaccgactaacagctgaagtaatgacagattgttgctgggtca
tatcagctttatcccttggtaattatatctgttttgtttcttgactctgtccaatcagagaata
aacatcatagtttcttggccactgaattagccaaaacacttaggaagaaatcacttaaatacct
ctggcttagaaatttttttcatgcacactgttggaatgtatgctaattgaacatgcaattgggga
agaaaaaattagaatgattttttgctatttctagtagaaagaaaatgtctgttttccaaagataa
tgttatacatcctattttgtaatttttttgaaaaaagttcaatgttcagttttccttagttttt
accttgttttctctataggtcagtatttctgtgaagcaaaaagatgccttttaccatgaattct
tgagtttacatcaataatattgtatattaaggggatcagaagtaggaaggaaaaaataagagat
agcagaggaaaaagaaaaacatttcctcttataacttctgaagtaatttgtaaaaaagatttgt
agagtcaatcatgtgtttaaattatttatcacaaacttaacatggaagatattccttttttaac
tttgtggtaacttctttgaagttatttagaaatatcctttggaacaattattttattgtctaat
aaatattgacttctcttgaattattttgcagactagtgagtctgtac
```

ACYL COENZYME A:CHOLESTEROL ACYLTRANSFERASE (ACAT)

REFERENCE TO RELATED APPLICATIONS

"This application is a divisional application of Ser. No. 08/121,057 filed on Sep. 10, 1993, now U.S. Pat. No. 5,484,727 which is a continuation-in-part of Ser. No. 07/959,950 filed Oct. 14, 1992, now abandoned. The contents of all of the aforementioned applications hereby incorporated by reference."

GOVERNMENT SUPPORT

The work leading to this invention was supported, in part, by research grants from The United States government.

BACKGROUND OF THE INVENTION

Acyl coenzyme A:cholesterol acyltransferase (ACAT) is an intracellular enzyme that uses cholesterol and fatty acyl-coenzyme A (CoA) to form cholesterol esters. Accumulation of cholesterol esters as cytoplasmic lipid droplets within cells of human aortic tissue is a characteristic feature of early lesions of atherosclerotic plaque. In intestines of vertebrate animals, the extent of absorption of dietary cholesterol can be shown to be significantly reduced by inhibiting intestinal ACAT activity. In livers of vertebrate animals, formation of lipoproteins require proper supply of cholesterol esters produced through the ACAT catalyzed reaction.

ACAT is a membrane-bound enzyme located in the endoplasmic reticulum of various tissues of animal and human cells. The enzyme has been localized to the rough endoplasmic reticulum in rat liver. It is highly regulated in many cell types and tissues, and it is believed to play an important role in cholesterol metabolism in various cells and tissues such as the small intestinal mucosa, hepatocytes, macrophages, and the steroid hormone-producing tissues (O'Brien, P. M. and Sliskovic, D. R. (1992) in Current Opinion in Therapeutic Patents; Cadigan, K. M., et al. (1988) *J. Biol. Chem.* 263:274–282; Cadigan, K. M., et al. (1989) *J. Cell Biol.* 108:2201–2210).

Although ACAT has been studied intensively, much remains to be learned about its molecular structure. The active site of the enzyme has been localized to the cytoplasmic surface of the microsomal vesicles in the rat liver, using a combination of detergent and protease treatments, but whether the enzyme spans the entire membrane has not yet been determined. Lichtenstein, A. H. and Brecher, P. (1980) *J. Biol. Chem.* 255:9098–9104. Recent chemical modification studies indicate that essential histidyl and sulfhydryl residues may reside at or near the active site of the enzyme. Studies of ACAT activities of rabbit tissues suggest the existence of different ACAT subtypes since various tissues have differing sensitivities to histidyl-modifying reagents. Kinnunen, P. M. et al. (1988) *Biochemistry* 27:7344–7350.

ACAT activity has been studied from ACAT solubilized and reconstituted from various cultured cells, including rat and pig liver cells. Although these procedures have allowed enzyme activity to be measured in a defined lipid environment, little progress has been made as yet in purifying the solubilized preparations. To date, no laboratory had succeeded in purifying ACAT to homogeneity with retention of biological activity.

SUMMARY OF THE INVENTION

This invention pertains to purified, biologically active acyl coenzyme A:cholesterol acyltransferase (ACAT) and to nucleic acid (DNA or RNA) encoding acyl coenzyme A:cholesterol acyltransferase. The nucleic acid, or a fragment thereof, may be ligated with an expression vector and transfected into cells to express acyl coenzyme A:cholesterol acyltransferase activity in intact cells and in cell-free extracts. The nucleic acid, or fragments thereof, are useful as probes, as primers for polymerase chain reactions, or as antisense constructs.

Cells containing the nucleic acid, or active fragment thereof, as well as various cell-free systems are useful for screening and testing chemical agents serving as specific ACAT inhibitors. Such ACAT inhibitors are desirable in the development of drugs serving as specific ACAT inhibitors for prevention and/or treatment of various cholesterol-related disorders.

In addition, the nucleotide sequence of the gene encoding ACAT enables the screening of human populations for abnormal human ACAT activities for disease diagnosis. This invention provides a basis for creating various transgenic animals including mice and rabbits that permanently express the human ACAT gene. Such animals can be used to screen and test various agents that inhibit human ACAT activity in a tissue specific or non-tissue-specific manner in intact animals. In addition, this invention provides a basis for creating transgenic animals including chickens, cows and pigs with permanently reduced ACAT activity. Animals with lower ACAT activity have much less body cholesterol ester content, and thus would offer the same nutritional value but with less dietary cholesterol intake to consumers.

BRIEF DESCRIPTION OF THE DRAWINGS

FIG. 3. Nucleotide sequence of cDNA C$_1$, as determined by double stranded DNA sequencing (SEQ ID NO:1).

FIG. 6. The nucleotide sequence of cDNA $K_1$ (SEQ ID NO:2(SEQID NO: 2). The region which overlaps with that of cDNA $C_1$ is underlined.

FIG. 9. The nucleotide and predicted amino acid sequences of cDNA $K_1$(SEQ ID NOs: 3 and 4; SEQ ID NO: 3 is an alternative embodiment of the sequence in FIG. 6). Nucleotide residues are numbered on the right; amino acid residues are numbered on the left with residue 1 being the putative initiator methionine. The 5 stretches SEQ OD NOs:5–9) of sequences sharing significant homology with firefly luciferase "signature sequences" regions 1, 2 or 3 (Babbitt et al., (1992) Biochemistry 31:5594–5604) are underlined in the protein coding region. Leucines involved in the potential leucine heptad motif are identified by asterisks. The potential N-linked glycosylation site is indicated by a double asterisk (amino acid residue 409). The two AATAAA sites are underlined in the 3'-untranslated region.

DETAILED DESCRIPTION

Figure 1:
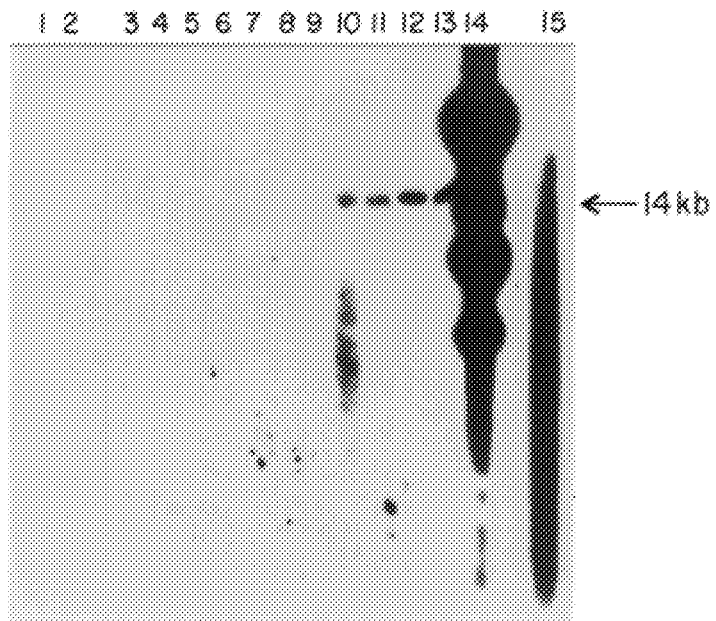
FIG. 1. Southern analysis of enzyme restricted genomic DNAs probed with $^{32}$P-gDNA G. Genomic DNAs were from 25-RA (lane 1), AC29 (lane 2), 29T2–8 Amph$^R$ 4,6, 8,10,11,12,16 (lanes 3–9), 29T1 (lane 10), 29T2–4 (lane 11), 29T2–8 (lane 12), 29T2–10 (lane 13), human fibroblast (lane 15). Genomic DNAs were digested with EcoRI and Hind III, run on a 0.8% agarose gel, transferred to a nylon filter and probed with radiolabeled gDNA G. Fifteen $\mu$g of genomic DNA was used for each sample except for human fibroblasts (5 mg). Lane 14 contains 10 $\mu$g of $\lambda$DNA (Hind III cut) as a size marker.

The enzyme acyl coenzyme A:cholesterol acyltransferase (ACAT) is an intracellular enzyme which previously had not been purified to homogeneity with retention of biological activity. This invention pertains to isolated, biologically active acyl coenzyme A:cholesterol transferase, or a biologically active portion thereof. As used herein, biological activity includes catalytic activity. ACAT has been shown to have amino acid sequences TNLIEKSASLDNGGCALTT, GRLVLEFSLLSYAF, GFGPTY, GYVAMKFAQVFGCF, and ARVLVLCUFNSILPGVL, SEQ ID NO:5, SEQ ID NO:6, SEQ ID NO:7, SEQ ID NO:8, and SEQ ID NO:9 and their functional equivalents, which are believed to be involved in catalytic activity. The enzyme, or active portion, is preferably human in origin.

The invention also pertains to the nucleic acid (DNA or RNA) encoding acyl coenzyme A:cholesterol acyltransferase and to the use of the nucleic acid to produce, by recombinant techniques, acyl coenzyme A:cholesterol acyltransferase.

One embodiment of the invention is the cDNA for human ACAT contained the clone $K_1$, or any derivative of this cDNA. This nucleotide sequence is shown in SEQ ID NO: 2. Variants of this ACAT nucleotide sequence are also within the scope of this invention. These include sequences substantially homologous to the sequence of SEG ID NO: 2. This includes sequences, such as those derived by mutagenesis, which have nucleotide insertions, deletions, substitutions, or other modifications, but which encode a catalytically active ACAT. The variants include fragments of the ACAT nucleotide sequence. As used herein, a fragment of the nucleotide sequence encoding human acyl coenzyme A:cholesterol acyltransferase refers to a nucleotide sequence having fewer nucleotides than the nucleotide sequence of the entire enzyme. Nucleic acid sequences used in any embodiment of this invention can be cDNA as described herein, or alternatively, can be any oligonucleotide sequence having all or a portion of a sequence represented herein, or their functional equivalents. Such oligonucleotide sequences can be produced chemically or mechanically using known techniques. A functional equivalent of an oligonucleotide sequence is one which is capable of hybridizing to a complementary oligonucleotide to which the sequences shown in the Sequence Listing, or fragment thereof, hybridizes, or a sequence complementary to either of the sequences shown in the Sequence Listing.

ACAT, or a portion of ACAT, can be produced by standard recombinant techniques using the nucleotide sequences of this invention. The nucleotide sequence encoding ACAT is inserted into an expression vector. A suitable host cell, such as a mammalian cell, is transformed with the vector, and the cell is cultured under conditions conducive to the production of the enzyme by the cell. ACAT, or a portion of ACAT, can be produced in other organisms, including bacteria, yeast, and insect cells, as well as various cell-free systems. A portion of ACAT expressed in these systems may express partial ACAT function, such as the ability to bind, inter alia, cholesterol, fatty acids, and coenzyme A, thus creating unique tools and assays for testing and screening for inhibitors which block these partial ACAT functions. these inhibitors would be genuine ACAT inhibitors.

The nucleotide sequence information contained in the cDNA encoding ACAT also provides crucial information concerning the catalytic mechanism of ACAT and provides investigators with a means for rational design of drugs serving as specific ACAT inhibitors. Such ACAT inhibitors are desirable for prevention and/or treatment of human hypercholesterolemia and human atherosclerosis. The nucleotide sequence information contained in the nucleic acid encoding ACAT enables design of various specific oligonucleotides as specific anti-sense DNAs or anti-sense RNAs, to inhibit human ACAT messenger RNAs, thereby to inhibit ACAT protein production, as described in more detail below.

The nucleic acid molecules of this invention can be used to produce primers for polymerase-mediated replication of nucleotide sequences encoding ACAT. Typically, the primer is a single stranded oligonucleotide substantially complementary to a portion of the ACAT sequence to be replicated. The primer will have a length sufficient to prime polymerase activity, generally a minimum of five to seven nucleotides, and typically from 16 to 30 nucleotides. Primers can be used in polymerase chain reaction (PCR) to amplify ACAT nucleotide sequences.

The nucleic acid molecules of this invention, and fragments thereof, are also useful as hybridization probes for library screenings to isolate and identify partial and/or full length cDNA or gDNA clones encoding ACAT genes from various animal species. Probes are generally labeled single stranded oligonucleotides substantially complementary to at least a portion of the ACAT nucleotide sequence. Hybridization reactions can be performed by standard techniques. Such probes can be used to identify different forms of human ACAT or ACAT from different animal species.

The probes and primers described above are useful as diagnostic tools to identify persons who have certain diseases, either acquired or genetically inherited, related to an abnormality in the ACAT gene or gene expression.

Nucleic acid molecules can be used to produce antisense constructs for inhibition of ACAT activity. In one embodiment, the oligonucleotide is an antisense oligonucleotide. The antisense oligonucleotide can be a normal oligonucleotide for an analogue of an oligonucleotide (e.g., phosphorothioate oligonucleotides, in which one of the phosphate oxygens is replaced by a sulfur atom) sufficiently stable to reach the target in effective concentrations. Antisense oligodeoxynucleotides can be prepared by standard synthetic procedures.

In another embodiment, the antisense construct is oligoribonucleotide. The antisense construct is produced by introducing the gene encoding the construct into a cell. For example, an ACAT nucleotide sequence can be placed in an expression vector in reverse orientation to generate an antisense transcript.

The antisense oligonucleotides can be designed to operate by different mechanisms of gene inhibition. Generally, these mechanisms involve the hybridization of the oligonucleotide to a specific RNA sequence, typically a messenger RNA. The targeted sequence can be located in the coding region of the RNA or it can be a signal sequence required for processing or translation of the RNA. Alternatively, the oligonucleotide may form a triple helix DNA structure, inhibiting transcription of the mRNA sequence.

The nucleic acid sequence of this invention can be used to produce transgenic animals either carrying human ACAT or having reduced levels of ACAT activity. Transgenic mammals, such as mice, expressing full or partial human ACAT activity can be easily created by methods well-documented in the art, for example those described in Leder et al., U.S. Pat. No. 4,736,866. One of ordinary skill in the art can prepare transgenic mammals by injecting the ACAT gene, or a portion thereof, into the germline of the mammal. Alternatively, the gene or gene fragment can be injected into the male pronucleus of the fertilized egg when the egg is at the single cell stage, prior to implanting the egg in the host female. Moreover, using similar methods, a transgenic animal, such as a chicken, cow, or pig, can be produced by, for example, transfecting germ cells with a nucleic acid sequence encoding an antisense construct which blocks ACAT expression. Transgenic mammals carrying those constructs would have decreased ACAT activity, and, as a result, lower body cholesterol levels. Such transgenic animals would offer the same nutritional values while decreasing consumers' dietary cholesterol intake.

The invention further comprises a stable mutant cell which lacks endogenous ACAT activity, and is transformed with a nucleic acid encoding human ACAT, such that the cell expresses activity of human ACAT, preferably at high levels, in intact cells and in cell-free extracts. The cell produces an excess of cholesterol ester, causing the cell to form detectable (e.g. visibly) cytoplasmic lipid droplets. These droplets disappear with inhibition of ACAT. This mutant cell containing the human ACAT gene can be used in an assay for agents, including antisense DNA and/or RNA, that inhibit human ACAT activity. The cell is exposed to the agent under conditions which allow the agent to be taken up into the cell, and the cell is examined for substantial disappearance of the lipid droplets. Substantial disappearance indicates inhibition of human acyl coenzyme A:cholesterol transferase. This invention also embraces any agents which inhibit ACAT identified by the above-described screening assay, or any other assay using the ACAT nucleic acid sequence, or fragments thereof.

The invention is illustrated further by the following exemplification.

EXEMPLIFICATION

Example I.

A. Preparing Human ACAT Genomic DNA Fragments

Chinese hamster ovary (CHO) cells are a fibroblast-like cell line in which cholesterol ester synthesis is highly regulated by exogenous sources of cholesterol, such as low density lipoprotein (LDL), and by endogenous cholesterol synthesis. The inventor and others previously developed an amphotericin B enrichment procedure, and reported the isolation of CHO cell mutants almost entirely lacking ACAT activity. All isolated mutants were found to belong to the same complementation group and possess a defect in the ACAT enzyme itself or in a factor needed for production of the enzyme (Cadigan, K. M., et al. (1988) *J. Biol. Chem.* 263:274–282).

Cells that regained the ability to synthesize cholesterol esters were isolated from the mutants described above. After populations of ACAT deficient mutant (AC29) were subjected to chemical mutagenesis, or transfected with human fibroblast whole genomic DNA, two revertants and one primary transfectant ($T_1$) were isolated. Isolation was achieved by virtue of the revertant cells' or transfectant cells' higher fluorescent intensities when stained with Nile Red, a stain specific for neutral lipids, including cholesterol esters.

Both revertants and transfectants regained large amounts of intracellular cholesterol ester and ACAT activity. However, heat inactivation experiments reveal that the enzyme activity of the transfectant cells has heat stability properties identical to those of human fibroblasts, while the ACAT activities of the revertants are similar to that of other Chinese hamster ovary cell lines. This demonstrates that the molecular lesion in the ACAT deficient mutants resides in the structural gene for the enzyme, and indicates that the transfectant cells corrected this lesion by acquiring and stably expressing a human gene encoding the human ACAT polypeptide.

Secondary transfectants (T2–4, T2–8, and T2–10) were isolated by transfection of ACAT deficient mutant cells with primary transfectant genomic DNA. Genomic Southern analysis of the secondary transfectants, using a probe specific for human DNA, revealed several distinct restriction fragments common to all the transfectants. These fragments were hypothesized to comprise part or all of the human ACAT gene (Cadigan, K. M., et al. (1989) *J. Cell Biol.* 108:2201–2210). These human gene fragments were isolated (see Section B below) and were used as the starting material for molecular cloning of the human ACAT cDNA of this invention.

Standard recombinant DNA techniques were employed, according to the methods known in the art and as described in Sambrook, J., et al. (1989) *Molecular Cloning: A Laboratory Manual,* 2nd ed., Cold Spring Harbor Laboratory, Cold Spring Harbor, N.Y. The use of λZAP, λDASH, pBluescript for library or recombinant plasmid constructions were following instructions manuals provided by Stratagene, Inc. The use of FAST-TRACK kit for mRNA isolation, of $pcDNA_1$ and $pcDNA_{neo}$ for library or recombinant plasmid constructions were following instruction manuals provided by Invitrogen Inc. Other biochemical assays and methods used here were all previously documented in Cadigan, K. M., et al. (1988) *J. Biol. Chem.* 263:274–282; Cadigan, K. M., et al. (1989) *J. Cell Biol.* 108:2201–2210; Hasan, M. T., et al. (1991) *Somatic Cell and Mol. Genetics* 17:413–517; Cadigan, K. M. and Chang, T. Y. (1988) *J. Lipid Res.* 29:1683–1692.

B. Isolating human ACAT cDNA $C_1$ Clone

A phage lambda (λDASH, from Stratagene, Inc.) library consisting of genomic DNA fragments of transfectant cell T2–8 was prepared and screened using the human-specific Alu-repetitive DNA as the probe prepared according to the method of Cadigan, K. M., et al. (1989) *J. Cell Biol.* 108:2201–2210. An Alu-positive, λ clone (designated as λG) containing an insert was isolated. The insert, designated as gDNA G, was determined to be approximately 14 kb in length. Insert gDNA G was labeled with $^{32}P$ and used as the probe in genomic Southern analyses of restriction-digested genomic DNAs of human skin fibroblasts, primary transfectant cell clone $T_1$, and of secondary transfectant cell clones T2–4, T2–8, and T2–10. Results (FIG. 1) show gDNA G is a specific, common-sized human DNA fragment present in the genomes of all four transfectant clones which exhibit human ACAT activity (Cadigan, K. M., et al. (1989) *J. Cell Biol.* 108:2201–2210). Fragment gDNA G was not found in the genomes of 25-RA cells or AC29 cells, which suggests that gDNA G may be part of the human ACAT genomic DNA.

TABLE 1

[$^3H$] Oleate Incorporated Into Cholesteryl Oleate in Intact Cells

| Cell Type | (% of 25RA) |
| --- | --- |
| 25-RA | 100.0* |
| 29T2-8 | 94.5 |
| 29T2-8Amph$^R$4 | 1.7 |
| 29T2-8Amph$^R$6 | 0.5 |
| 29T2-8Amph$^R$8 | 1.1 |
| 29T2-8Amph$^R$10 | 0.8 |
| 29T2-8Amph$^R$11 | 0.6 |
| 29T2-8Amph$^R$12 | 0.0 |
| 29T2-8Amph$^R$16 | 0.9 |
| 29T2-8Amph$^R$17 | 1.1 |
| 29T2-8Amph$^R$18 | 1.2 |

*100% = 7529 dpm/min/mg

To demonstrate the accuracy of this theory, nine individual ACAT deficient cells were isolated using the secondary transfectant cell T2–8 as the parental cell. The T2–8 cell was found to be very sensitive to amphotericin B killing. Using the same procedure as previously described for isolating ACAT deficient mutants from 25-RA cells (Cadigan, K. M., et al. (1988) *J. Biol. Chem.* 263:274–282), nine independent cell clones (designated as T2–8 $^{Ampho\ R4}$, T2–8 $^{Ampho.\ R6}$; etc.) were obtained from approximately 10 ×10$^6$ T2–8 cells. These clones are found to be devoid of ACAT activity when analyzed by $^3H$-oleate pulse in intact cells, as shown in Table 1.

Figure 2:
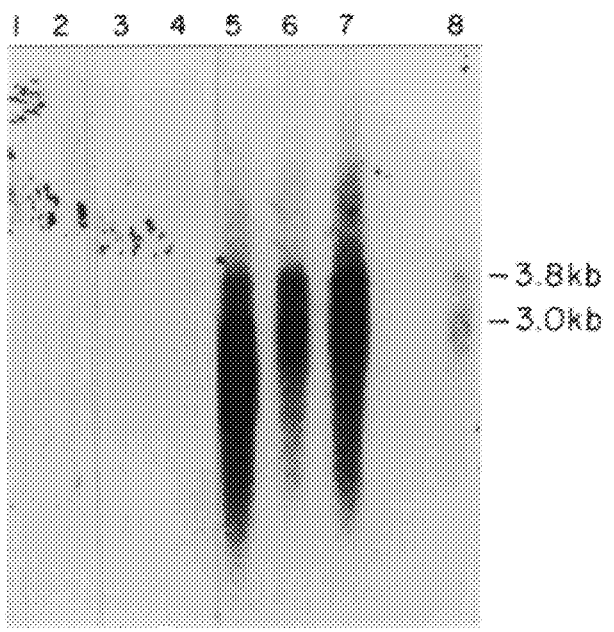
FIG. 2. Northern analysis of polyA$^+$mRNAs probed with $^{32}$P-gDNA G$_2$. PolyA$^+$mRNAs were prepared using FAST-TRACK (Invitrogen, Inc.) from confluent monolayer cells grown in media with 10% fetal calf serum of AC29 (lane 1), 25-RA (lane 2), T2–8 Amph$^R$4 (lane 3), T2–8 Amph$^R$10 (lane 4), T2–4, 8, 10 (lanes 5–7), and human A431 cells (lane 8). RNAs were run on a denaturing gel and blotted onto a nylon filter, cross-linked with UV light. Approx. 15 $\mu$g of RNA was used per lane. A control experiment showed that the same blot probed with $^{32}$P-actin cDNA provided a strong and sharp signal at the 1.9 kb region with approximately equal intensity for all 8 lanes.

Southern analyses (FIG. 1, lanes 3–9) using gDNA G as the probe showed that, in contrast to the parental T2–8 cells, none of these independent cell clones contains DNA fragment G as part of their genomes. This demonstrates 100% concordance between the presence/absence of DNA fragment G in the cell genome and the presence/absence of human ACAT activity in various CHO cells, and strongly supports the proposition that gDNA G is part of the human ACAT genomic DNA.

gDNA fragment G was digested with HinfI. The resulting 1.2 kb fragment designated as gDNA $G_2$, which was found to be devoid of Alu-repetitive DNA, was isolated and cloned into the phagemid vector pBluescript (Stratagene). Fragment gDNA $G_2$ was found to contain at least one exonic element, since it strongly hybridized (particularly at the 3.8 kb and 3.0 kb regions) with polyA$^+$mRNAs of discrete sizes prepared from all of the human ACAT positive transfectant cells, and from human epidermal carcinoma A431 cells. The results of the Northern analysis of those polyA$^+$mRNAs is shown in FIG. 2.

Figure 4:
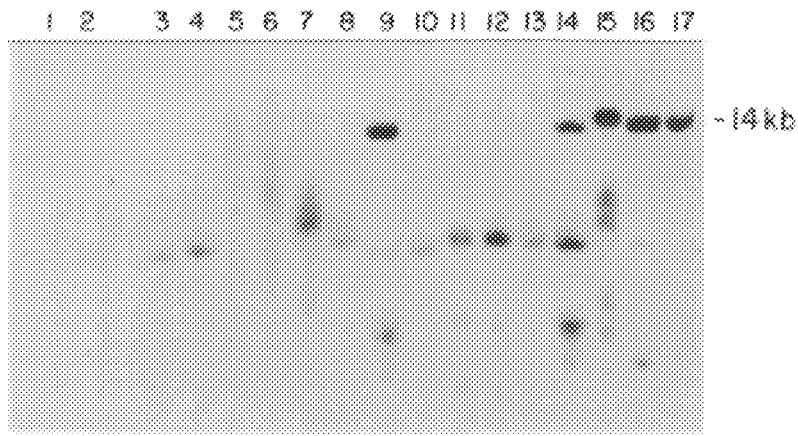
FIG. 4. Southern analysis of enzyme restricted genomic DNAs probed with $^{32}$P-cDNA C$_1$. Genomic DNAs were from 25-RA (lane 2), AC29 (lane 3), T2–8 Amph$^R$4, 6, 8, 10, 11, 12, 16, 17, 18 (lanes 4–8, 10–13), 29T1 (lane 9), 29T2–4, 8, 10 (lanes 14, 15, 16), human fibroblast (lane 17). Lane 1 contains 10 $\mu$g of gDNA (Hind III cut) as a size marker. Genomic DNAs were digested and analyzed in the same manner as described in FIG. 2, except the $^{32}$P-probe was cDNA C$_1$.
Figure 5A:
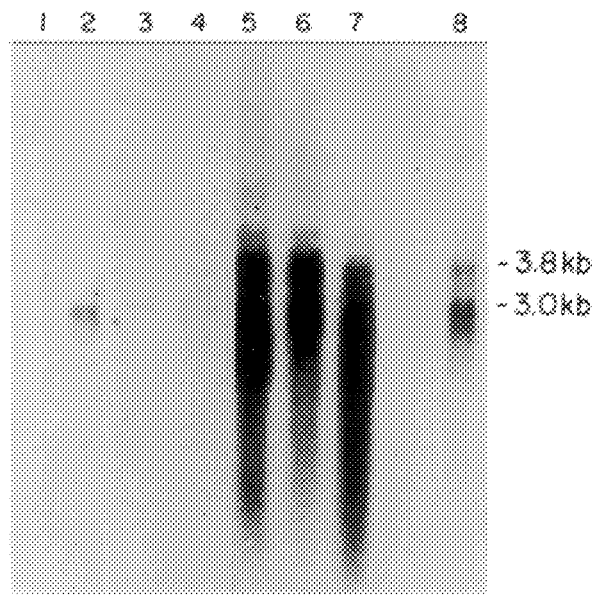
FIG. 5. Northern analysis of polyA+mRNAs probed with $^{32}$P-cDNA C$_1$. A duplicate blot prepared in an identical manner as described in FIG. 2 was probed with either $^{32}$P-cDNA $C_{1\ (A),\ or}$ $^{32}$P-actin cDNA (B).
Figure 5B:
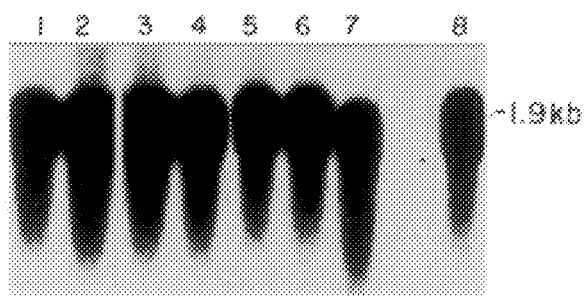

A cDNA library was prepared using polyA$^+$mRNAs of T2–8 cells using pcDNA$_1$ (from Invitrogen, Inc.) as the vector. This library was screened with $^{32}P$ gDNA $G_2$. A single cDNA clone (size=1006 bps) was identified, designated as cDNA $C_1$, and sequenced. As shown in FIG. 3 and the Sequence Listing, the nucleotide sequence contains a single, uninterrupted open-reading frame for a predicted polypeptide of 335 amino acids. Extensive search for nucleotide sequence homology between $C_1$ DNA and other DNAs of known sequences in several DNA sequence data banks reveals that the $C_1$ sequence has never been reported in the art. Genomic Southern analyses, FIG. 4, show that $^{32}P$-$C_1$ DNA strongly hybridizes with the same 14-kb genomic DNA fragment recognized by gDNA G in all the transfectant cell DNAs, and in human fibroblast DNAs. Northern analyses, shown in FIG. 5, demonstrate that $^{32}P$-$C_1$ DNA strongly hybridizes with the same polyA$^+$mRNA species as recognized by the gDNA $G_2$ fragment in transfectant cell RNAs. These hybridization signals were absent in CHO cells devoid of human ACAT activity (FIG. 4, lanes 2–8 and 10–13; FIG. 5, lanes 1–4), consistent with the interpretation that $C_1$ DNA is part of the human ACAT cDNA. Clone $C_1$ DNA was ligated in two opposite orientations with the mammalian expression vector pcDNA$_{neo}$ (from Invitrogen), and then transfected into AC29 cells. These experiments repeatedly failed to produce functional complementation of ACAT deficiency in AC29 cells, thus indicating that $C_1$ DNA does not contain sufficient coding sequences to express human ACAT activity in CHO cells.

Example I.

A phage lambda library (in λZAP; Stratagene) containing cDNAs of human macrophage cell line THP-1 cells was obtained from Dr. T. Kodama of Tokyo University in Japan as a generous gift. (Preparation and use of this particular library is described in Matsumoto, et al. (1990) *Proc. Natl. Acad. Sci.* 87:9133–9137). This library was screened using both gDNA $G_2$ and cDNA $C_1$ as the probe. A single clone was identified which strongly hybridizes with both $G_2$ and $C_1$ probes. This clone, designated as cDNA $K_1$, is approximately 4.1 kb in length.

The entire $K_1$ nucleotide sequence has been completed, with 98% to 99% certainty, and is shown in FIG. 6 and in the Sequence Listing. Uncertain nucleotides are represented by the letter N. The $K_1$ nucleotide comprises a 1006-bp nucleotide sequence (underlined) which shares 100% homology with that of the DNA $C_1$ sequence shown in FIG. 3. $K_1$ cDNA can be stably propagated as an insert in the phagemid pBluescript.

To demonstrate that $K_1$ DNA complements ACAT deficiency in AC29 cells, the pBluescript plasmid containing $K_1$ DNA as the insert (designated as p$K_1$) was digested with enzymes NotI and EcoRV, to release the intact $K_1$ DNA insert free of NotI and EcoRV sites from the vector. The DNA mixture was ligated with a NotI-EcoRV linearized pcDNA$_1$ vector for the purpose of ligating $K_1$ DNA with the CMV promoter in proper orientation. The ligated DNA mixture was directly transfected into AC29 cells. Appropriate control transfections, using various DNA mixtures without $K_1$ DNA or without pcDNA$_1$ were performed in parallel. The result (Table 2) indicates that DNA $K_1$ is necessary to provide large increases in rate of cholesteryl ester synthesis in AC29 cells, in both transient and stable transfection experiments.

TABLE 2

Transfection of Various DNA Mixtures Into ACAT Deficient Mutant (Clone AC29)

| DNA Mixture | Relative Rate of Cholesterol Ester Synthesis In Intact Cells | | Relative Rate of Phospholipid Synthesis In Intact Cells |
|---|---|---|---|
| | A. Transient Transfection | B. Stable Transfection | |
| None | 1.0* | 1.0** | 1.0*** |
| pSV2 neo | 1.0 | 1.5 | 1.2 |
| pSV2 neo + pBluescript | 0.9 | 1.3 | 1.7 |
| pSV2 neo + pcDNA$_1$ | 1.1 | 1.6 | 0.9 |
| pSV2 neo + pBluescript + pcDNA$_1$ | 1.0 | 1.0 | 1.6 |
| pSV2 neo + pBluescript + K$_1$ | 2.4 | 8.6 | 1.4 |
| pSV2 neo + pBluescript + pcDNA$_1$ + K$_1$ | 6.0 | 21.8**** | 1.0 |

*1.0 = 134 dpm/min/mg
**1.0 = 80 dpm/min/mg
***1.0 = 23 × 10$^2$ dpm/min/mg; measured only in stable transfectant cells
****12.4% of value found in 25-RA cells In the experiments reported in Table 2, DNA transfection of AC29 cells was accomplished according to the method of Hasan et al. ((1991) *Somatic Cell and Mol. Genetics* 17:413–517). AC29 cells plated at 0.3×10$^6$ cells/25 cm$^2$ flask in medium A were grown for 24 h before transfection. Each transfection was performed in triplicate, and included supercoiled plasmid pSV2$_{neo}$ (at 0.7 μg/flask) along with indicated DNA mixtures (which totaled 17.5 μg/flask). Each indicated plasmid was sequentially cut with EcoRV and NotI, salt precipitated, and redissolved in sterile water.

For the DNA mixture involving pBluescript +pcDNA$_1$, or pBluescript +pcDNA$_1$ +K$_1$, ligation took place as follows: 50 μg pcDNA$_1$ was ligated with either 12.5 μg pBluescript, or with 25 μg pK$_1$ (cut with EcoRV and NotI to release K$_1$ insert from vector) in 20 μl volume using 3400 units of T4 DNA ligase (New England Biolab) at 16° C. overnight. The ligated DNA mixtures were salt precipitated, redissolved in sterile water and used directly in transfection experiments.

To measure cholesterol ester synthesis in transient transfectant cells, transfected cells were grown in medium A for 2 days, then in medium A +500 μg/ml G418 for one more day, and were subjected to $^3$H-oleate pulse assay in duplicate flasks. To measure cholesterol ester synthesis in stable transfectant cells, cells after transfection were grown in medium A for 2 days, then in medium A+500 μg/ml G418 for 14 days. The G418 resistant cells were then placed in medium A in duplicate flasks, and were subjected to $^3$H-oleate pulse assay.

In a separate experiment, DNA mixtures of pBluescript+ pcDNA$_{neo}$, or of pBluescript+pcDNA$_{neo+K1}$ were treated, ligated, and used for stable transfection in an identical manner to that described in Table 2. Stable transfectant cells (resistant to 500 μg/ml G418 toxicity) were isolated and subjected to $^3$H-oleate pulse assay. Results very similar to those shown in Table 2 were obtained: While the transfectant clones resulting from the former DNA mixture only provided basal values, those resulting from the latter DNA mixture provided large increase (by approximately 10-fold) in rate of cholesterol ester synthesis as compared to the basal value found in AC29 cells.

In the stable transfectant cell populations containing pcDNA$_1$ and K$_1$ DNA, or containing pcDNA$_{neo\ and\ K1}$ DNA, a great deal of heterogeneity was observed in cytoplasmic cholesteryl ester contents, present as lipid droplets, in various cell clones. This can be visually detected by examination of cells under phase-contrast microscopy. That this is so appears to be due to variability of expression of the transfected K$_1$ gene in different clones.

Example III: Stable Transfectant 14e

The stably transfected cells described above were cloned by cloning rings. Eight independently cloned transfectant cells were evaluated for their rates of cholesterol ester synthesis in intact cells and in vitro by reconstituted ACAT assay. The result (shown in Table 3) indicates that one clone, identified as 14e, expresses the highest ACAT activity in intact cells and in vitro. Its ACAT activity is higher than those found in the transfectant clone T2–8 obtained previously through total human genomic DNA transfection experiments. A second stable transfectant clone (4b), obtained using the ligated DNA mixture of pcDNA$_{neo}$+ pBluescript+K$_1$, expresses significant ACAT activity, but this activity is less than that measured in the T2–8 cells.

TABLE 3

Rates of Cholesterol Ester Synthesis of Individual AC29 Clones Stably Transfected with K1 cDNA

| Cell Type | In Intact Cells (by Oleate Pulse) | In Vitro (By Reconstituted ACAT Assay) |
|---|---|---|
| AC29 | 1.0* | 1.0** |
| 29K1-10 | 0.7 | 1.0 |
| 29K1-11 | 1.1 | 1.0 |
| 29K1-12 | 0.8 | 1.1 |
| 29K1-6 | 1.1 | 1.9 |
| 29K1-13 | 5.4 | 3.1 |
| 29K1-5 | 0.9 | 4.3 |
| 29K1-4b | 42.4 | 13.6 |
| 29K1-14e | 82.4 | 23.3 |
| 29T2-8 | 70.6 | 16.1 |
| 25-RA | 84.2 | 44.4 |

*1.0 = 133 dpm/min/mg
**1.0 = 4 pmole/min/mg

In the experiments reported in Table 3, Clones 29K$_1$-10, 11, 12, 13, and 14e were isolated from stable transfectant cells described in Table 2 using pSV2$_{neo}$+pBluescript+K$_1$ as the DNA mixture; clones 29 K$_1$.4b, 29 K$_1$-5, 29 K$_1$-6 were isolated from stable transfectant cells using pBluescript+ pcDNA$_{neo}$+K$_1$, performed in a separate experiment in similar manner as described in Table 2; clones 14a, 14d, and 14e were isolated from stable transfectant cells described in Table 2 using pSV2$_{neo}$+pBluescript+pcDNA$_1$+K$_1$ as the DNA mixture. The oleate pulse assay and in vitro reconstituted ACAT activity assay were performed in duplicate as described earlier (Cadigan, K. M., et al. (1988) *J Biol. Chem.* 263:274–282; Cadigan, K. M., et al. (1989) *J. Cell Biol.* 108:2201–2210).

Figure 7A:
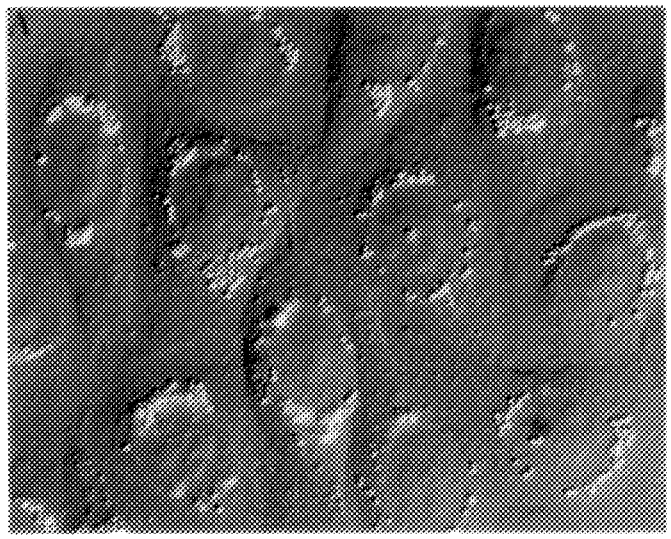
FIG. 7. 25-RA cells (A), AC29 cells (C) the stable transfectant cells 29 $K_1$-14e treated with (D) or without (B) ACAT inhibitor 58-035 viewed with differential-interference contrast microscopy. Cells were plated and processed for differential-interference contrast microscopic viewing by the same procedure as described in Cadigan, K. M., et al. (1989) J. Cell Biol. 108:2201–2210. In (D), cells were treated with 58-035 at 400 ng/ml for 36 h.
Figure 7B:
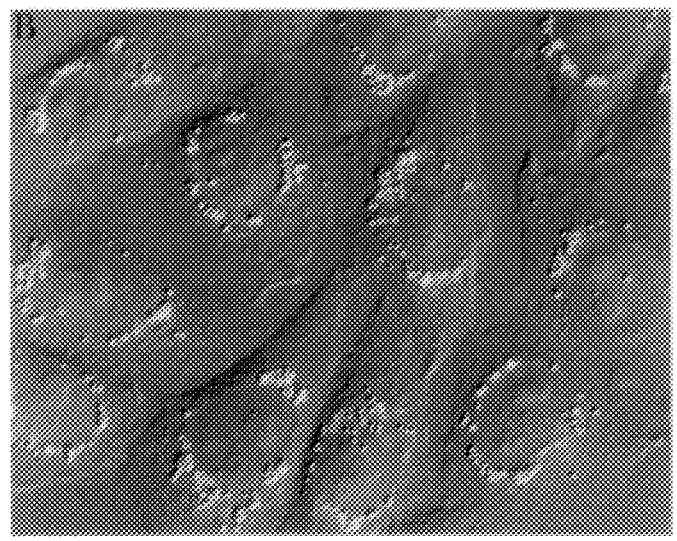
Figure 7C:
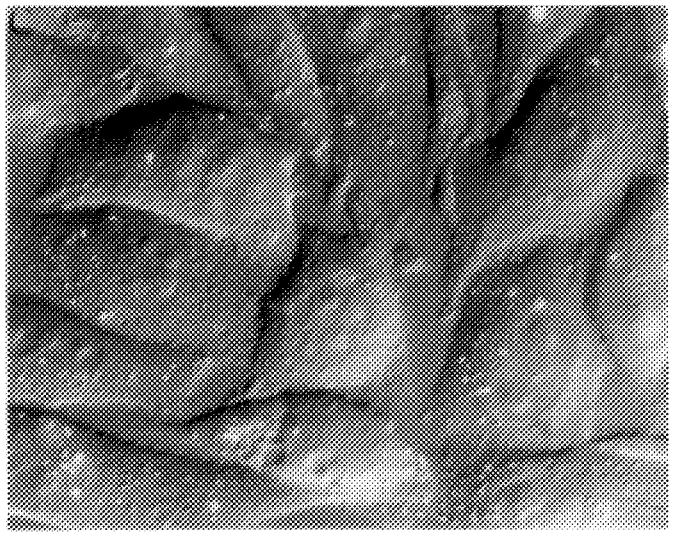

In 14e cells, numerous cytoplasmic lipid droplets are visible under the microscope (FIG. 7B). When treated with an ACAT inhibitor, specifically 58-035 at 400 ng/ml for 36 h, most of the lipid droplets in 14e cells disappear (FIG. 7D), indicating that these are cholesteryl ester droplets. For comparison purposes, photos of 25-RA cells, which contain ACAT of CHO origin, and AC29 cells, which are deficient in ACAT activity, as viewed under the microscope, are provided in FIG. 7A and 7C. The cloned populations of 14e cells can be continuously grown in culture for at least two months without losing this distinct phenotype.

As was previously reported, the biochemical characteristics of ACAT activities present in the crude extracts of cultured human cells differs from that in CHO cells. Cadigan, K. M. et al. (1989) *J. Cell Biol.* 108:2201–2210: In reconstituted vesicles of defined lipid composition, the CHO cell ACAT activity exhibits a significantly greater thermolability at 45° C. than that of human cell ACAT activity. Based on this criterion, primary and secondary genomic ACAT transfectant cells (29T1, 29T2–4, 29T2–8, and 29T2–10) were determined to contain ACAT activities of human origin. Further investigation, by heat inactivation of the ACAT activities expressed in stable cDNA $K_1$ transfectant clones 14e and 4b, and comparison with that expressed in 25-RA cells and in T2–8 cells shows that the ACAT inactivation rates in 14e cells and 4b cells are the same as that of T2–8 cells, which is considerably slower than that found in 25-RA cells. This indicates that the ACAT activities expressed in $14_e$ cells and $4_b$ cells are of human origin. This result invalidates the alternative interpretation: that the $K_1$ cDNA was human cDNA which, upon transfection in AC29 cells, reactivated the CHO ACAT activity. If this were the case, the ACAT activity expressed in cells 14e and 4b would have behaved like that expressed in 25-RA cells, i.e., the CHO ACAT, in the heat inactivation study.

Figure 7D:
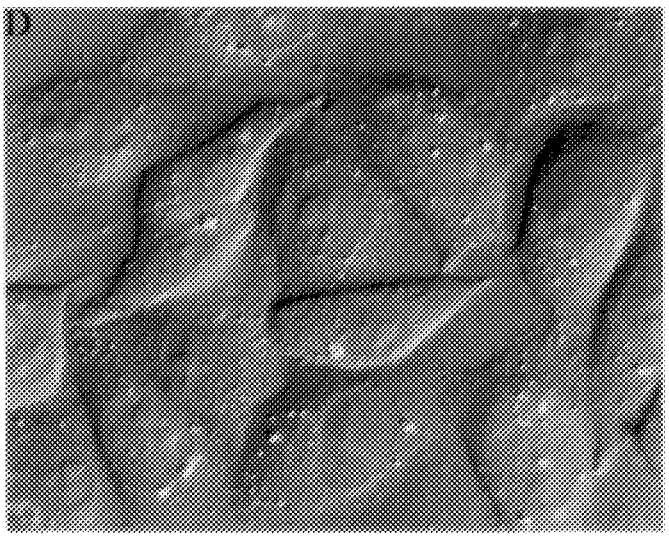
Figure 8:
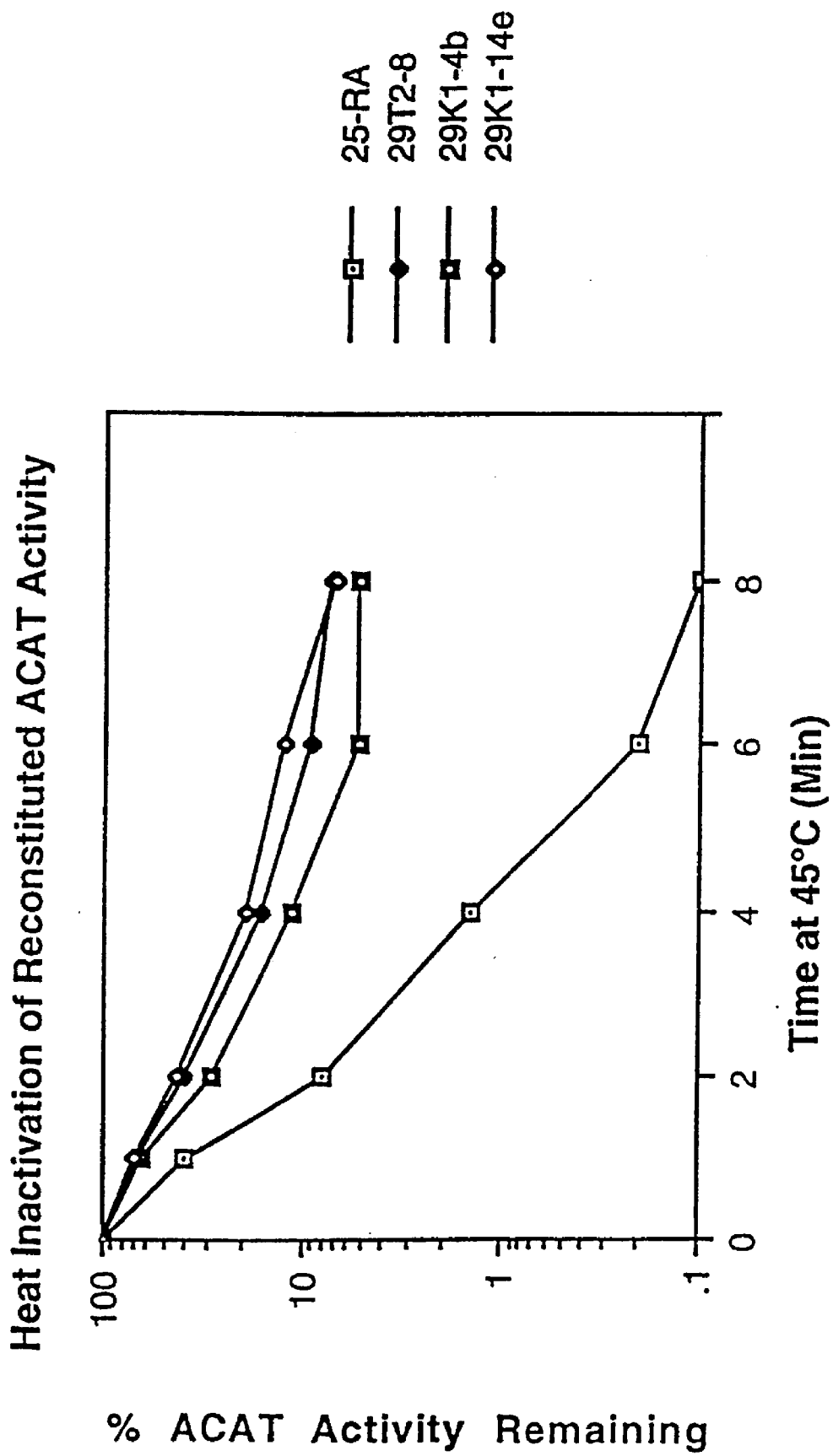
FIG. 8. Heat inactivation of reconstituted ACAT activity from 25-RA (symbol=open square), 29 T2–8 (symbol=closed diamond), 29 $K_1$-4b (symbol=closed square), and 29 $K_1$-14e (symbol=partially open diamond). Cells were grown in 162 cm$^2$ flasks in medium A to confluence. They were harvested, and the cell extracts were reconstituted according to the procedure of Cadigan and Chang (1988) J. Lipid Res. 29:1683–1692. The reconstituted samples were incubated at 45° C. at indicated times, then placed on ice prior to assay for enzyme activity. The control activities for 25-RA, 29 T2–8, 29 $K_1$-4b, and 29 $K_1$14e were 228, 73, 43, and 109 pmoles/min per mg respectively.

This cell clone can effectively be used as a tool to screen drugs and anitisense constructs serving as human ACAT inhibitors. The numerous cytoplasmic lipid droplets in 14e cells that are visible under the microscope provide an elegant test for evaluating potential ACAT inhibitors. Specifically, when 14e cells are treated with an ACAT inhibitor, the lipid droplets essentially disappear, as illustrated in FIG. 7D. A simple, visual method for testing and screening potential human ACAT inhibitors in cultured cells is thus provided. Those skilled in the art will recognize that this embodiment is not limited to 14e cells, and can be used with any stable transfectant cell line that hyper expresses the ACAT gene, or a fragment thereof, for example, the 29K-4b or $29T_2$ cell lines. Those skilled in the art will also recognize that the visual detection of intracellular cholesteryl esters present in 14e cells, or other cell line capable of hyper expressing ACAT, could be achieved by means other than standard microscopy, such as phase-contrast microscopy, fluorescent dye staining followed by fluorescent microscopy, among others. The speed of detection may also be enhanced by coupling a rapid scanning mechanism to the microscopic apparatus.

Example IV. 1.7 kb $K_1$ cDNA Encoding Human ACAT

A fragment of the 4.0 kb $K_1$ cDNA was discovered that spans the entire predicted protein coding region of ACAT. It is the 1.7 kb Sal I-Hind III fragment, spanning nucleotide residues 1302-3050 of $K_1$.

Subcloning the 1.7 kb fragment into the pcDNA1$_{neo}$ vector, in both directions, produced plasmids designated pcDNA1$_{neo}$-K$_{1.7kb\ sense}$ and pcDNA1$_{neo}$-K$_{1.7kb\ antisense}$. To demonstrate ACAT expression, the plasmids, together with pcDNA$_{neo}$ as a control, were transiently transfected into AC29 cells. As shown in Table 4, transfection of pcDNA1$_{neo}$-K$_{1.7kb\ sense}$ dramatically increased the rate of cholesterol ester synthesis in AC29 cells, with values equal to 60% of those found in 25-RA cells. The plasmid minimally increased the rate of phospholipid synthesis. Control plasmids exhibited no similar effects. Plasmid pcDNA1$_{neo}$-K$_{1.7kb\ sense}$ also increased the rate of cholesterol ester synthesis in stable transfectant cells, approximately 20% of values found in 25-RA cells, without altering the rates of phospholipid synthesis.

TABLE 4

Transient Transfection of Plasmids Containing pcDNA1$_{neo}$ Vector and K1$_{1.7kb}$ cDNA as Insert into ACAT Deficient Mutant (Clone AC29)

| DNA Mixture | Relative Rate of Cholesterol Ester Synthesis In Intact Cells | | Relative Rate of Phospholipid Synthesis In Intact Cells | |
| --- | --- | --- | --- | --- |
| | A. Third day after Transfection | B. Fifth Day after Transfection | A. Third day after Transfection | B. Fifth day after Transfection |
| pcDNA1$_{neo}$ | 1.0[a] | 1.0[b] | 1.0[c] | 1.0[d] |
| pcDNA1$_{neo}$-K1$_{1.7kb}$ (antisense) | 0.9 | .07 | 1.0 | 1.0 |
| pcDNA1$_{neo}$-K1$_{1.7kb}$ (sense) | 103 | 91* | 1.7 | 1.4 |

[a]1.0 = 29 dpm/min/mg
[b]1.0 = 45 dmp/min/mg
[c]1.0 = 1404 dpm/min/mg
[d]1.0 = 164 dpm/min/mg
*60.5% of value found in 25-RA The method of Hason et al. ((1991) Somatic Cell and Mol. Genetics 17:413–417) was used to perform transfection. 0.3×10$^6$ cells per 25 cm$^2$ flask were seeded in medium A for 24 h. 3 ml of fresh medium A with 100 $\mu$M Chloroquine was then added for 2 h before the transfection. For each flask, 3 $\mu$g of pcDNA1$_{neo}$ DNA or 5 $\mu$g of pcDNA1$_{neo}$-K$_{1.7kb}$ DNA was used in transfection. Incubation was at 37° C. for 16 h. Transfection cells were grown in medium A +500 $\mu$g.ml G418 for 3 or 5 days and were then subjected to $^3$H-oleate pulse assay in duplicate flasks. The construction of pcDNA1$_{neo}$-K$_{1.7kb}$ plasmids was described in Experimental Procedures.

As shown in FIG. 4., the $K_1$ cDNA contains a single open reading frame (ORF) (residues 1397-3046) 1650 bps in length and a predicted 64,805 dalton protein. This ORF is designated as ACAT $K_1$ protein. The second and third nucleotides before the putative first ATG codon and the one after it conformed to the Kozak sequences (Kozak, 1984). An in-frame stop codon was found 150 nucleotides upstream from the first ATG codon.

Hydrophobicity analysis of the hypothetical ACAT $K_1$ protein indicates that it contains at least two potential transmembrane α-helices located at amino acids 132–155 and 460–483 (FIG. 7). This analysis supports the conclusion that ACAT $K_1$ is an integral membrane protein. The polypeptide regions at amino acids 215–235, 320–340, and 355–380 are also very hydrophobic, yet these regions seem to be rich in β-sheet structure (panel B of FIG. 7), therefore, these regions may not contain transmembrane helices. One potential N-glycosylation site (Gavel and von Heijne, (1990) *Protein Engineering* 3:433–442) was identified (indicated by the symbol ** in FIG. 4). In contrast, the classic phosphorylation sites recognized by different protein kinases including c-AMP-dependent protein kinase and protein kinase C (reviewed in Kemp and Pearson, (1990) *Trends in Biochem. Sci.* 15: 342–346), could not be clearly identified. In addition, the proposed motif (Jackson and Peterson, (1990) *The EMBO J.* 9: 3153–3162) for retention of certain transmembrane proteins in the endoplasmic reticulum as well as the motif (Petrou et al., (1993) *Trends in Biochem. Sci.* 18:41–42) for the fatty acid binding domain of certain intracellular lipid binding proteins could not be identified.

Tissue Distribution of ACAT $K_1$ Gene Transcripts

The human tissue distribution of $K_1$ gene transcripts was examined using $^{32}$P-cDNA C1 as the probe. The results (not shown) indicate that it cross-hybridized with poly(A)$^+$RNAs of various discrete sizes, with strong signals at approx. 3 and 4 kb and with weak signals at approx. 4.7 and 7.4 kb. While the intensities varied, these signals were found in poly (A)$^+$RNAs of virtually all of the tissues reported here.

Example V. Homology With Other Enzymes

Figure 9A:
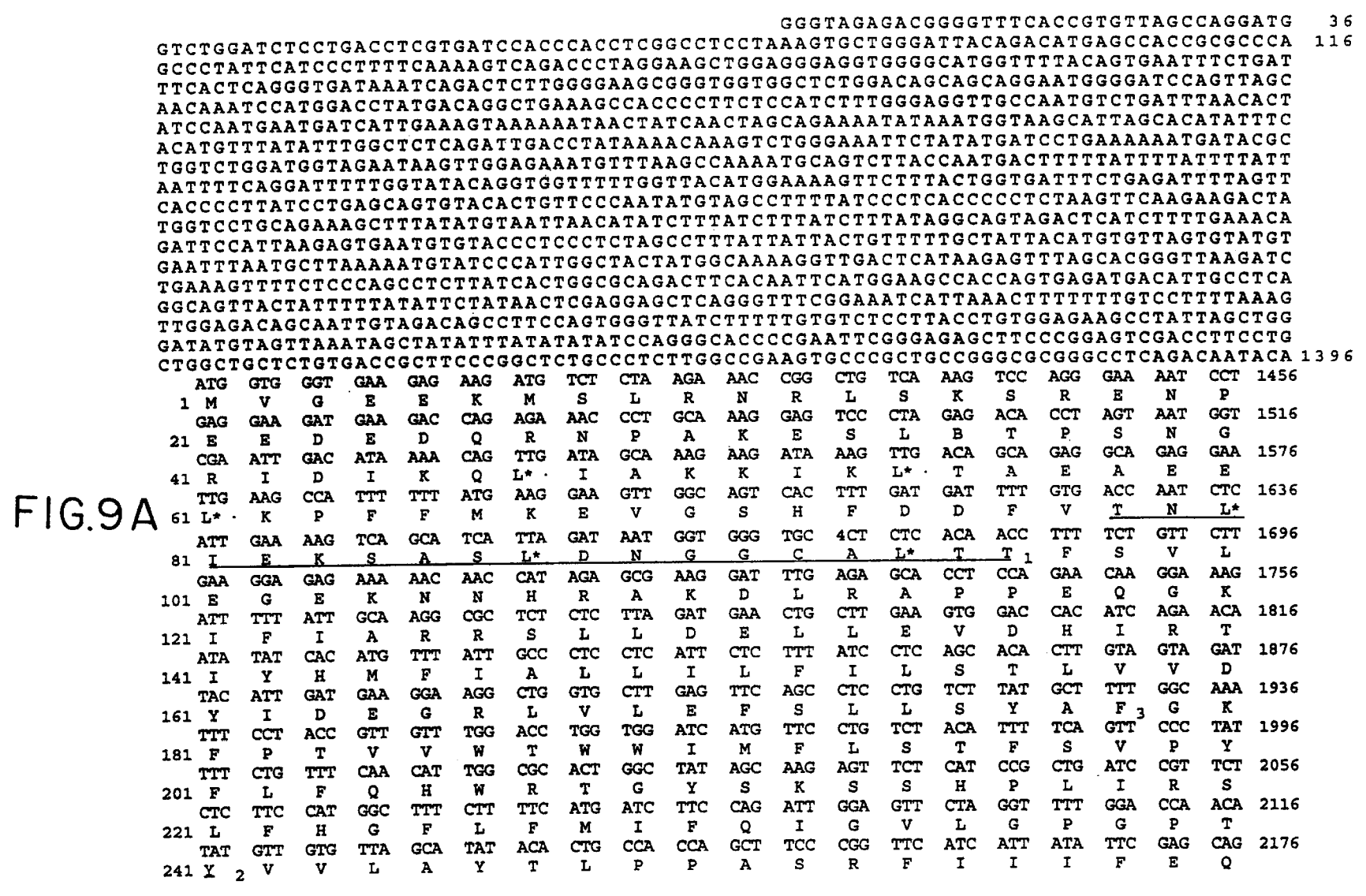
Figure 9B:
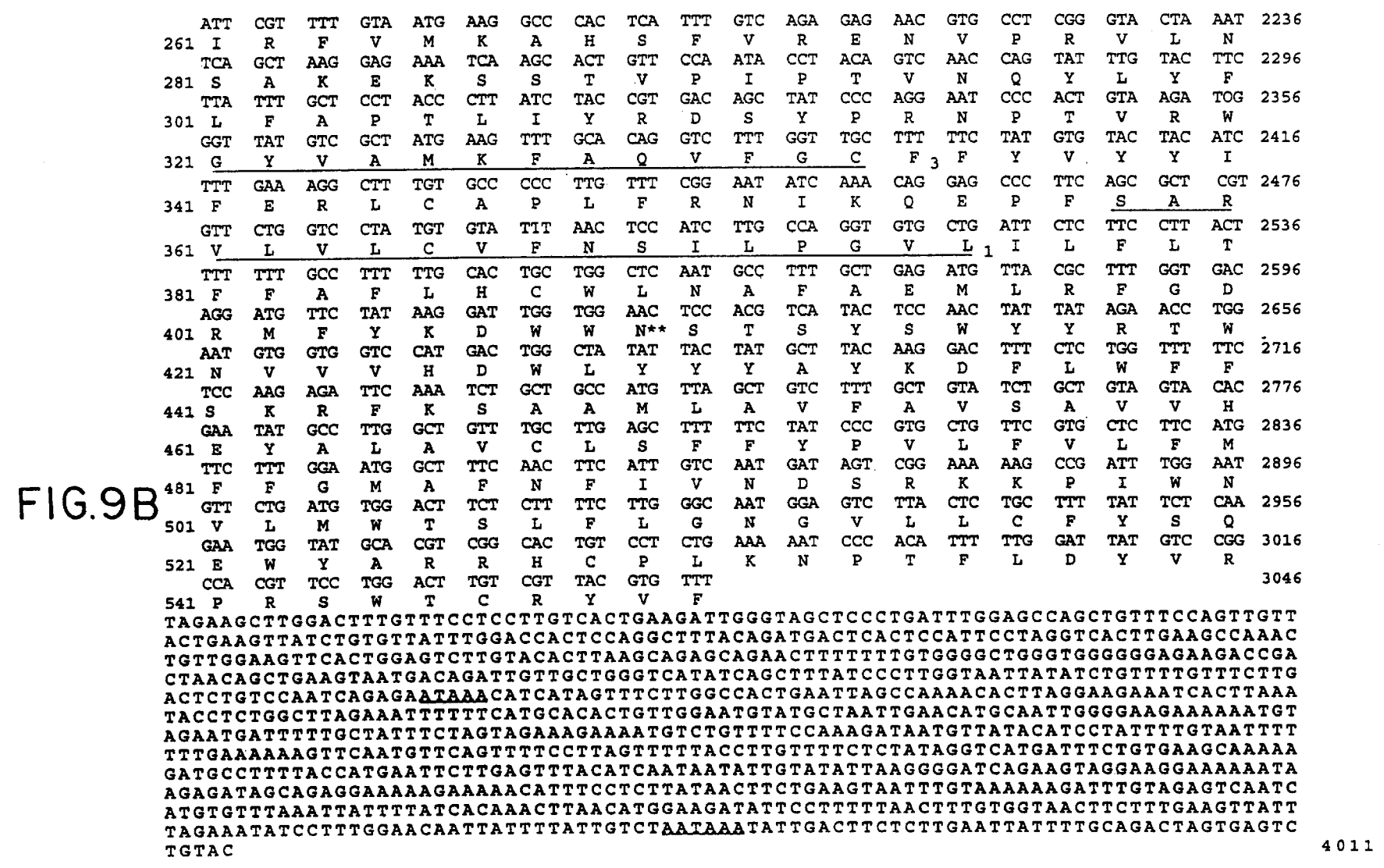

Protein homology analysis shows that the entire predicted ACAT $K_1$ protein sequence shares a 48% homology with human fatty acid ligase (Abe et al., (1992) *J. Biochem.* 111:123–129). In addition, further analysis shows that the predicted $K_1$ protein contains five separate stretches of linear sequences (TNLIEKSASLDNGGCALTT, GRLVLEFSLLSYAF, GFGPTY, GYVAMKFAQVFGCF, and ARVLVLCVFNSILPGVL, SEQ ID NO:5, SEQ ID NO:6, SEQ ID NO:7, SEQ ID NO:8, and SEQ ID NO:9 underlined in the protein coding region of FIG. 9) which share significant homology (42%, 57%, 80%, 57%, and 58% respectively, based on firefly luciferase sequences) with the newly identified "signature sequences" (Babbitt et al., (1992) *Biochemistry* 31: 5594–5604). These signature sequences include three separate segments of peptides and are present in at least twelve different enzymes including firefly luciferase and fatty acid ligase. These enzymes participate in various metabolic functions, and show one common feature—all are involved in the catalysis of acyl adenylate formation followed by acyl thioester formation and subsequent acyl transfer. This analysis suggests that these enzymes share common catalytic mechanisms, and these "signature sequences" constitute part(s) of the active site(s) of these enzymes. Within the ACAT $K_1$ protein sequence, two different stretches of peptides share homology with the "signature sequence" region #1 (amino acids 193–212 of luciferase), one stretch of peptides shares homology with signature sequence region #2 (amino acids 338–344 of luciferase), while two other stretches of peptides shared homology with the "signature sequence" region #3 (amino acids 338–401 of luciferase).

This finding is important for at least two reasons. First, it suggests that, in addition to functioning as a fatty acyl coenzyme A:cholesterol acyltransferase, the ACAT enzyme may also possess enzymatic activity mechanistically very similar to that of fatty acid: coenzyme A ligase, as well as those of the other enzymes listed in Table 1 of the Babbitt et al. article, *supra*. Second, this information provides an important clue for designing specific ACAT inhibitors based on known catalytic mechanisms utilized by these enzymes. For example, it should now be possible to design specific ACAT inhibitors based on structural characteristics of various inhibitors already known to inhibit the active site(s) of any of the enzymes listed in Table 1 of the Babbitt, et al. article, *supra*.

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. Isolated and purified human acyl coenzyme A:cholesterol acyltransferase (ACAT), or a fragment thereof, retaining enzymatic ACAT activity.

2. The isolated and purified human acyl coenzyme A:cholesterol acyltransferase of claim 1 produced by recombinant DNA techniques from the nucleic acid sequence selected from the group consisting of the nucleotide sequences shown in SEQ ID NO: 1, SEQ ID NO: 2, and SEQ ID NO: 3, and fragments thereof, retaining enzymatic activity.

3. The isolated and purified enzymatically active acyl coenzyme A:cholesterol acyltransferase of claim 1 having an amino acid sequence containing a linear sequence selected from the group consisting of SEQ ID NO: 5, SEQ ID NO: 6, SEQ ID NO: 7, SEQ ID NO: 8, and SEQ ID NO: 9, and a fragment of said ACAT retaining enzymatic activity.

4. The isolated biologically active acyl coenzyme A:cholesterol acyltransferase of claim 1 produced by recombinant DNA techniques from the nucleic acid sequence shown in SEQ ID NO:3 and a fragment thereof retaining enzymatic activity.

5. Purified enzymatically active acyl coenzyme A:cholesterol acyltransferase having the amino acid sequence shown in SEQ ID NO: 4, and fragments thereof retaining enzymatic activity.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 996 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GAAACCCTGC  AAAGGAGTCC  CTAGAGACAC  CTAGTAATGG  TCGAATTGAC  ATAAAACAGT      60

TGATAGCAAA  GAAGATAAAG  TTGACAGCAG  AGGCAGAGGA  ATTGAAGCCA  TTTTTTATGA     120
```

```
AGGAAGTTGG CAGTCACTTT GATGATTTTG TGACCAATCT CATTGAAAAG TCAGCATCAT    180
TAGATAATGG TGGGTGCGCT CTCACAACCT TTTCTGTTCT TGAAGGAGAG AAAAACAACC    240
ATAGAGCGAA GGATTTGAGA GCACCTCCAG AACAAGGAAA GATTTTTATT GCAAGGCGCT    300
CTCTCTTAGA TGAACTGCTT GAAGTGGACC ACATCAGAAC AATATATCAC ATGTTTATTG    360
CCCTCCTCAT TCTCTTTATC CTCAGCACAC TTGTAGTAGA TTACATTGAT GAAGGAAGGC    420
TGGTGCTTGC AAGTTACGCC TCCTGTCTTA TGCATTTTGG CAAATTTCCT ACCGTTGTTT    480
GGACCTGGTG GATCATGTTC CTGTCTACAT TTTCAGTTCC CTATTTCTG TTTCAACATT     540
GGCGCACTGG CTATAGCAAG AGTTCTCATC CGCTGATCCG TTCTCTCTTC CATGGCTTTC    600
TTTTCATGAT CTTCCAGATT GGAGTTCTAG GTTTTGGACC AACATATGTT GTGTTAGCAT    660
ATCCTGCCAC CAGCTTCCCG GTTCATCATT ATTCGAGCAG ATCGTTTGT AATGAAGGCC     720
CACTCATTTG TCAGAGAGAA CGTGCCTCGG GTACTAATTC AGCTAAGGAG AAATCAAGCA    780
CTGTTCCAAT ACCTACAGTC AACCAGTATT TGTACTTCTT ATTTGCTCCT ACCCTTATCT    840
ACCGTGACAG CTATCCCAGG AATCCACTG TAAGATGGGG TTATGTTGCT ATGAAGTTTG     900
CACAGGTCTT TGGTTGCTTT TTCTATGTGT ACTACATCTT TGAAAGGCTT TGTGCCCCT     960
TGTTTCGGAA TATCAAACAG GAGCCCTTCA GCGCTC                              996
```

(2) INFORMATION FOR SEQ ID NO:2:

(i) SEQUENCE CHARACTERISTICS:
    (A) LENGTH: 4079 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:2:

```
GGGTAGAGAC GGGGTTTCAC CGTGTTAGCC AGGATGGTCT GGATCTCCTG ACCTCGTGAT    60
CCACCCACCT CGGCCTCCTA AAGTGCTGGG ATTACAGACA TGAGCCACCG CGCCCAGCCC    120
TATTCATCCC TTTTCAAAAG TCAGACCCTA GGAAGCTGGA GGGAGGTGGG GCATGGTTTT    180
ACAGTGAATT TCTGATTTCA CTCAGGGTGA TAAATCAGAC TCTTGGGGAA GCGGTGGTG    240
GCTCTGGACA GCAGCAGGAA TGGGGATCCA GTTAGCAACA AATCCATGGA CCTATGACAG    300
GCTGAAAGCC ACCCCTTCTC CATCTTTGGG AGGTTGCCAA TGTCTGATTT AACACTATCC    360
AATGAATGAT CATTGAAAGT AAAAAATAAC TATCAACTAG CAGAAAATAT AAATGGTAAG    420
CATTAGCACA TATTTCACAT GTTTATATTT GGCTCTCAGA TTGACCTATA AACAAAGTC     480
TGGGAAATTC TATATGATCC TGAAAAAATG ATACGCTGGT CTGGATGGTA GAATAAGTTG    540
GAGAAATGTT TAAGCCAAAA TGCAGTCTTA CCAATGACTT TTATTTTAT TTATTAATT      600
TTCAGGATTT TTGGTATACA GGTGGTTTTT GGTTACATGG AAAAGTTCTT TACTGGTGAT    660
TTCTGAGATT TTAGTTCACC CCTTATCCTG AGCAGTGTAC ACTGTTCCCA ATATGTAGCC    720
TTTTATCCCT CACCCCCTCT AAGTTCAAGA AGACTATGGT CCTGCAGAAA GCTTTATATG    780
TAATTAACAT ATCTTTATCT TTATCTTTAT AGGCAGTAGA CTCATCTTTT GAAACAGATT    840
CCATTAAGAG TGAATGTGTA CCCTCCCTCT AGCCTTTATT ATTACTGTTT TGCTATTAC     900
ATGTGTTAGT GTATGTGAAT TTAATGCTTA AAAATGTATC CCATTGGCTA CTATGGCAAA    960
AGGTTGACTC ATAAGAGTTT AGCACGGGTT AAGATCTGAA AGTTTTCTNN CCCAGCCTCT    1020
TATCACTGGC NAGACTTCAC AATTCATGGA AGCCACCAGT GAGATGACAT TAGCACGGGT    1080
```

| | | | | | | |
|---|---|---|---|---|---|---|
| AGTCGATTTG | CAGCCTCTTA | TCACTGNNNN | AGACTTCACA | ATTCATGGAA | CAGGAATGAC | 1140 |
| ATTTCGCTCA | GGCAGTTACT | GTTTTTATAT | TCTATAACTC | GAGGAGCTCA | GGGCTTTCGG | 1200 |
| AAATCATTAA | ACTTTCCTTG | TCCTTTTAAA | GTTGGAGCCA | GCAATTGTAG | ACAGCCTTCC | 1260 |
| AGTGGGTTAT | CTTTTTGTGT | CTCCTTACCT | GTGGAGAAGC | CTATTAGCTG | GATATATTAT | 1320 |
| TAAATAGCTA | TATTTATATA | TATCCAGGGC | ACCCGAATTC | GGGAGAGCTT | CCCGGAGTCG | 1380 |
| ACCTTCCTGC | TGGCTGCTCT | GTGACGCTTC | CCGCTCTGCC | CTCTTGGCCG | AAGTCGCGCT | 1440 |
| GCCGGGCGCG | GGCCTCAGAC | AATACAATGG | TGGGTGAAGA | GAAGATGTCT | CTAAGAAACC | 1500 |
| GGCTGTCAAA | GTCCAGGGAA | AATCCTGAGG | AAGATGAAGA | CCAGGAGAAA | CCCTGCAAAG | 1560 |
| GAGTCCCTAG | AGACACCTAG | TAATGGTCGA | ATTGACATAA | AACAGTTGAT | AGCAAAGAAG | 1620 |
| ATAAAGTTGA | CAGCAGAGGC | AGAGGAATTG | AAGCCATTTT | TTATGAAGGA | AGTTGGCAGT | 1680 |
| CACTTTGATG | ATTTGTGAC | CAATCTCATT | GAAAAGTCAG | CATCATTAGA | TAATGGTGGG | 1740 |
| TGCGCTCTCA | CAACCTTTTC | TGTTCTTGAA | GGAGAGAAAA | ACAACCATAG | AGCGAAGGAT | 1800 |
| TTGAGAGCAC | CTCCAGAACA | AGGAAAGATT | TTTATTGCAA | GGCGCTCTCT | CTTAGATGAA | 1860 |
| CTGCTTGAAG | TGGACCACAT | CAGAACAATA | TATCACATGT | TTATTGCCCT | CCTCATTCTC | 1920 |
| TTTATCCTCA | GCACACTTGT | AGTAGATTAC | ATTGATGAAG | GAAGGCTGGT | GCTTGCAAGT | 1980 |
| TACGCCTCCT | GTCTTATGCA | TTTTGGCAAA | TTTCCTACCG | TTGTTTGGAC | CTGGTGGATC | 2040 |
| ATGTTCCTGT | CTACATTTTC | AGTTCCCTAT | TTTCTGTTTC | AACATTGGCG | CACTGGCTAT | 2100 |
| AGCAAGAGTT | CTCATCCGCT | GATCCGTTCT | CTCTTCCATG | GCTTTCTTTT | CATGATCTTC | 2160 |
| CAGATTGGAG | TTCTAGGTTT | TGGACCAACA | TATGTTGTGT | TAGCATATCC | TGCCACCAGC | 2220 |
| TTCCCGGTTC | ATCATTATTC | GAGCAGATCG | TTTTGTAATG | AAGGCCCACT | CATTTGTCAG | 2280 |
| AGAGAACGTG | CCTCGGGTAC | TAATTCAGCT | AAGGAGAAAT | CAAGCACTGT | TCCAATACCT | 2340 |
| ACAGTCAACC | AGTATTTGTA | CTTCTTATTT | GCTCCTACCC | TTATCTACCG | TGACAGCTAT | 2400 |
| CCCAGGAATC | CCACTGTAAG | ATGGGGTTAT | GTTGCTATGA | AGTTTGCACA | GGTCTTTGGT | 2460 |
| TGCTTTTTCT | ATGTGTACTA | CATCTTTGAA | AGGCTTTGTG | CCCCCTTGTT | TCGGAATATC | 2520 |
| AAACAGGAGC | CCTTCAGCGC | TCGTGTTCTG | GTCCTATGTG | TATTTAACTC | CATCTTGCCA | 2580 |
| GGTGTGCTGA | TTCTCTTCCT | TACTTTTTTT | GCCTTTTGC | ACTGCTGGCT | CAATGCCTTT | 2640 |
| GCTGAGATGT | TACGCTTTGG | TGACAGGATG | TTCTATAAGG | ATTGGTGGAA | CTCCACGTCA | 2700 |
| TACTCCAACT | ATTATAGAAC | CTGGAATGTG | GTGGTCCATG | ACTGGCTATA | TTACTATGCT | 2760 |
| TACAAGGACT | TTCTCTGGTT | TTTCTCCAAG | AGATTCAAAT | CTGCTGCCAT | GTTAGCTGTC | 2820 |
| TTTGCTGTAT | CTGCTGTAGT | ACACGAATAT | GCCTTGGCTG | TTTGCTTGAG | CTTTTTCTAT | 2880 |
| CCCGTGCTGT | TCGTGCTCTT | CATGTTCTTT | GGAATGGCTT | TCAACTTCAT | TGTCAATGAT | 2940 |
| AGTCGGAAAA | AGCCGATTTG | GAATGTTCTG | ATGTGGACTT | CTCTTTTCTT | GGGCAATGGA | 3000 |
| GTCTTACTCT | GCTTTTATTC | TCAAGAATGG | TATGCACGTC | GGCACTGTAC | CTCTGAAAAA | 3060 |
| TCCCACATTT | TTGGATTATG | TCCTGTCACG | TTCCTGGACT | TGTCGTTACG | TGTTTTAGAA | 3120 |
| GCTTGGACTT | TGTTTCCTCC | TTGTCACTGA | AGATTGGGTA | GCTCCCTGAT | TGGAGCCAG | 3180 |
| CTGTTTCCAG | TTGTTACTGA | AGTTATCTGT | GTTATTGGA | CCACTCCAGG | CTTTACAGAT | 3240 |
| GACTCACTCC | ATTCCTAGGT | CACTTGAAGC | CAAACTGTTG | GAAGTTCACT | GGAGTCTTGT | 3300 |
| ACACTTAAGC | AGAGGAGAAC | TTTTTTTGTG | GGGCTGGGTG | GGGGGAGAAG | ACCGACTAAC | 3360 |
| AGCTGAAGTA | ATGACAGATT | GTTGCTGGGT | CATATCAGCT | TTATCCCTTG | GTAATTATAT | 3420 |
| CTGTTTTGTT | TCTTGACTCT | GTCCAATCAG | AGAATAAACA | TCATAGTTTC | TTGGCCACTG | 3480 |

| | | | | | | |
|---|---|---|---|---|---|---|
| AATTAGCCAA | AACACTTAGG | AAGAAATCAC | TTAAATACCT | CTGGCTTAGA | AATTTTTTCA | 3540 |
| TGCACACTGT | TGGAATGTAT | GCTAATTGAA | CATGCAATTG | GGGAAGAAAA | AATTAGAATG | 3600 |
| ATTTTTGCTA | TTTCTAGTAG | AAAGAAATG | TCTGTTTTCC | AAAGATAATG | TTATACATCC | 3660 |
| TATTTTGTAA | TTTTTTTGAA | AAAAGTTCAA | TGTTCAGTTT | TCCTTAGTTT | TTACCTTGTT | 3720 |
| TTCTCTATAG | GTCAGTATTT | CTGTGAAGCA | AAAAGATGCC | TTTTACCATG | AATTCTTGAG | 3780 |
| TTTACATCAA | TAATATTGTA | TATTAAGGGG | ATCAGAAGTA | GGAAGGAAAA | AATAAGAGAT | 3840 |
| AGCAGAGGAA | AAAGAAAAAC | ATTTCCTCTT | ATAACTTCTG | AAGTAATTTG | TAAAAAAGAT | 3900 |
| TTGTAGAGTC | AATCATGTGT | TTAAATTATT | TTATCACAAA | CTTAACATGG | AAGATATTCC | 3960 |
| TTTTTAACTT | TGTGGTAACT | TCTTTGAAGT | TATTTAGAAA | TATCCTTTGG | AACAATTATT | 4020 |
| TTATTGTCTA | ATAAATATTG | ACTTCTCTTG | AATTATTTTG | CAGACTAGTG | AGTCTGTAC | 4079 |

(2) INFORMATION FOR SEQ ID NO:3:

(i) SEQUENCE CHARACTERISTICS:
        (A) LENGTH: 4011 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1397..3046

(xi) SEQUENCE DESCRIPTION: SEQ ID NO:3:

| | | | | | | |
|---|---|---|---|---|---|---|
| GGGTAGAGAC | GGGGTTTCAC | CGTGTTAGCC | AGGATGGTCT | GGATCTCCTG | ACCTCGTGAT | 60 |
| CCACCCACCT | CGGCCTCCTA | AAGTGCTGGG | ATTACAGACA | TGAGCCACCG | CGCCCAGCCC | 120 |
| TATTCATCCC | TTTTCAAAAG | TCAGACCCTA | GGAAGCTGGA | GGGAGGTGGG | GCATGGTTTT | 180 |
| ACAGTGAATT | TCTGATTTCA | CTCAGGGTGA | TAAATCAGAC | TCTTGGGGAA | GCGGGTGGTG | 240 |
| GCTCTGGACA | GCAGCAGGAA | TGGGGATCCA | GTTAGCAACA | AATCCATGGA | CCTATGACAG | 300 |
| GCTGAAAGCC | ACCCCTTCTC | CATCTTTGGG | AGGTTGCCAA | TGTCTGATTT | AACACTATCC | 360 |
| AATGAATGAT | CATTGAAAGT | AAAAAATAAC | TATCAACTAG | CAGAAAATAT | AAATGGTAAG | 420 |
| CATTAGCACA | TATTTCACAT | GTTTATATTT | GGCTCTCAGA | TTGACCTATA | AAACAAAGTC | 480 |
| TGGGAAATTC | TATATGATCC | TGAAAAAATG | ATACGCTGGT | CTGGATGGTA | GAATAAGTTG | 540 |
| GAGAAATGTT | TAAGCCAAAA | TGCAGTCTTA | CCAATGACTT | TTTATTTTAT | TTTATTAATT | 600 |
| TTCAGGATTT | TTGGTATACA | GGTGGTTTTT | GGTTACATGG | AAAAGTTCTT | TACTGGTGAT | 660 |
| TTCTGAGATT | TTAGTTCACC | CCTTATCCTG | AGCAGTGTAC | ACTGTTCCCA | ATATGTAGCC | 720 |
| TTTTATCCCT | CACCCCCTCT | AAGTTCAAGA | AGACTATGGT | CCTGCAGAAA | GCTTTATATG | 780 |
| TAATTAACAT | ATCTTTATCT | TTATCTTTAT | AGGCAGTAGA | CTCATCTTTT | GAAACAGATT | 840 |
| CCATTAAGAG | TGAATGTGTA | CCCTCCCTCT | AGCCTTTATT | ATTACTGTTT | TTGCTATTAC | 900 |
| ATGTGTTAGT | GTATGTGAAT | TTAATGCTTA | AAAATGTATC | CCATTGGCTA | CTATGGCAAA | 960 |
| AGGTTGACTC | ATAAGAGTTT | AGCACGGGTT | AAGATCTGAA | AGTTTCTCC | CAGCCTCTTA | 1020 |
| TCACTGGCGC | AGACTTCACA | ATTCATGGAA | GCCACCAGTG | AGATGACATT | GCCTCAGGCA | 1080 |
| GTTACTATTT | TTATATTCTA | TAACTCGAGG | AGCTCAGGGT | TTCGGAAATC | ATTAAACTTT | 1140 |
| TTTTGTCCTT | TTAAAGTTGG | AGACAGCAAT | TGTAGACAGC | CTTCCAGTGG | GTTATCTTTT | 1200 |
| TGTGTCTCCT | TACCTGTGGA | GAAGCCTATT | AGCTGGGATA | TGTAGTTAAA | TAGCTATATT | 1260 |
| TATATATATC | CAGGGCACCC | CGAATTCGGG | AGAGCTTCCC | GGAGTCGACC | TTCCTGCTGG | 1320 |

```
CTGCTCTGTG ACCGCTTCCC GGCTCTGCCC TCTTGGCCGA AGTGCCCGCT GCCGGGCGCG            1380

GGCCTCAGAC AATACA ATG GTG GGT GAA GAG AAG ATG TCT CTA AGA AAC               1429
              Met Val Gly Glu Glu Lys Met Ser Leu Arg Asn
               1               5                  10

CGG CTG TCA AAG TCC AGG GAA AAT CCT GAG GAA GAT GAA GAC CAG AGA              1477
Arg Leu Ser Lys Ser Arg Glu Asn Pro Glu Glu Asp Glu Asp Gln Arg
            15                  20                  25

AAC CCT GCA AAG GAG TCC CTA GAG ACA CCT AGT AAT GGT CGA ATT GAC              1525
Asn Pro Ala Lys Glu Ser Leu Glu Thr Pro Ser Asn Gly Arg Ile Asp
        30                  35                  40

ATA AAA CAG TTG ATA GCA AAG AAG ATA AAG TTG ACA GCA GAG GCA GAG              1573
Ile Lys Gln Leu Ile Ala Lys Lys Ile Lys Leu Thr Ala Glu Ala Glu
    45                  50                  55

GAA TTG AAG CCA TTT TTT ATG AAG GAA GTT GGC AGT CAC TTT GAT GAT              1621
Glu Leu Lys Pro Phe Phe Met Lys Glu Val Gly Ser His Phe Asp Asp
60                  65                  70                  75

TTT GTG ACC AAT CTC ATT GAA AAG TCA GCA TCA TTA GAT AAT GGT GGG              1669
Phe Val Thr Asn Leu Ile Glu Lys Ser Ala Ser Leu Asp Asn Gly Gly
                80                  85                  90

TGC GCT CTC ACA ACC TTT TCT GTT CTT GAA GGA GAG AAA AAC AAC CAT              1717
Cys Ala Leu Thr Thr Phe Ser Val Leu Glu Gly Glu Lys Asn Asn His
            95                  100                 105

AGA GCG AAG GAT TTG AGA GCA CCT CCA GAA CAA GGA AAG ATT TTT ATT              1765
Arg Ala Lys Asp Leu Arg Ala Pro Pro Glu Gln Gly Lys Ile Phe Ile
        110                 115                 120

GCA AGG CGC TCT CTC TTA GAT GAA CTG CTT GAA GGT GTG GAC CAC ATC AGA          1813
Ala Arg Arg Ser Leu Leu Asp Glu Leu Leu Glu Val Asp His Ile Arg
    125                 130                 135

ACA ATA TAT CAC ATG TTT ATT GCC CTC CTC ATT CTC TTT ATC CTC AGC              1861
Thr Ile Tyr His Met Phe Ile Ala Leu Leu Ile Leu Phe Ile Leu Ser
140                 145                 150                 155

ACA CTT GTA GTA GAT TAC ATT GAT GAA GGA AGG CTG GTG CTT GAG TTC              1909
Thr Leu Val Val Asp Tyr Ile Asp Glu Gly Arg Leu Val Leu Glu Phe
                160                 165                 170

AGC CTC CTG TCT TAT GCT TTT GGC AAA TTT CCT ACC GTT GTT TGG ACC              1957
Ser Leu Leu Ser Tyr Ala Phe Gly Lys Phe Pro Thr Val Val Trp Thr
            175                 180                 185

TGG TGG ATC ATG TTC CTG TCT ACA TTT TCA GTT CCC TAT TTT CTG TTT              2005
Trp Trp Ile Met Phe Leu Ser Thr Phe Ser Val Pro Tyr Phe Leu Phe
        190                 195                 200

CAA CAT TGG CGC ACT GGC TAT AGC AAG AGT TCT CAT CCG CTG ATC CGT              2053
Gln His Trp Arg Thr Gly Tyr Ser Lys Ser Ser His Pro Leu Ile Arg
    205                 210                 215

TCT CTC TTC CAT GGC TTT CTT TTC ATG ATC TTC CAG ATT GGA GTT CTA              2101
Ser Leu Phe His Gly Phe Leu Phe Met Ile Phe Gln Ile Gly Val Leu
220                 225                 230                 235

GGT TTT GGA CCA ACA TAT GTT GTG TTA GCA TAT ACA CTG CCA CCA GCT              2149
Gly Phe Gly Pro Thr Tyr Val Val Leu Ala Tyr Thr Leu Pro Pro Ala
                240                 245                 250

TCC CGG TTC ATC ATT ATA TTC GAG CAG ATT CGT TTT GTA ATG AAG GCC              2197
Ser Arg Phe Ile Ile Ile Phe Glu Gln Ile Arg Phe Val Met Lys Ala
            255                 260                 265

CAC TCA TTT GTC AGA GAG AAC GTG CCT CGG GTA CTA AAT TCA GCT AAG              2245
His Ser Phe Val Arg Glu Asn Val Pro Arg Val Leu Asn Ser Ala Lys
        270                 275                 280

GAG AAA TCA AGC ACT GTT CCA ATA CCT ACA GTC AAC CAG TAT TTG TAC              2293
Glu Lys Ser Ser Thr Val Pro Ile Pro Thr Val Asn Gln Tyr Leu Tyr
    285                 290                 295

TTC TTA TTT GCT CCT ACC CTT ATC TAC CGT GAC AGC TAT CCC AGG AAT              2341
```

```
Phe  Leu  Phe  Ala  Pro  Thr  Leu  Ile  Tyr  Arg  Asp  Ser  Tyr  Pro  Arg  Asn
300            305                           310                           315

CCC  ACT  GTA  AGA  TGG  GGT  TAT  GTC  GCT  ATG  AAG  TTT  GCA  CAG  GTC  TTT         2389
Pro  Thr  Val  Arg  Trp  Gly  Tyr  Val  Ala  Met  Lys  Phe  Ala  Gln  Val  Phe
               320                      325                           330

GGT  TGC  TTT  TTC  TAT  GTG  TAC  TAC  ATC  TTT  GAA  AGG  CTT  TGT  GCC  CCC         2437
Gly  Cys  Phe  Phe  Tyr  Val  Tyr  Tyr  Ile  Phe  Glu  Arg  Leu  Cys  Ala  Pro
               335                      340                      345

TTG  TTT  CGG  AAT  ATC  AAA  CAG  GAG  CCC  TTC  AGC  GCT  CGT  GTT  CTG  GTC         2485
Leu  Phe  Arg  Asn  Ile  Lys  Gln  Glu  Pro  Phe  Ser  Ala  Arg  Val  Leu  Val
               350                 355                           360

CTA  TGT  GTA  TTT  AAC  TCC  ATC  TTG  CCA  GGT  GTG  CTG  ATT  CTC  TTC  CTT         2533
Leu  Cys  Val  Phe  Asn  Ser  Ile  Leu  Pro  Gly  Val  Leu  Ile  Leu  Phe  Leu
          365                      370                           375

ACT  TTT  TTT  GCC  TTT  TTG  CAC  TGC  TGG  CTC  AAT  GCC  TTT  GCT  GAG  ATG         2581
Thr  Phe  Phe  Ala  Phe  Leu  His  Cys  Trp  Leu  Asn  Ala  Phe  Ala  Glu  Met
380                      385                      390                      395

TTA  CGC  TTT  GGT  GAC  AGG  ATG  TTC  TAT  AAG  GAT  TGG  TGG  AAC  TCC  ACG         2629
Leu  Arg  Phe  Gly  Asp  Arg  Met  Phe  Tyr  Lys  Asp  Trp  Trp  Asn  Ser  Thr
               400                      405                           410

TCA  TAC  TCC  AAC  TAT  TAT  AGA  ACC  TGG  AAT  GTG  GTG  GTC  CAT  GAC  TGG         2677
Ser  Tyr  Ser  Asn  Tyr  Tyr  Arg  Thr  Trp  Asn  Val  Val  Val  His  Asp  Trp
               415                      420                           425

CTA  TAT  TAC  TAT  GCT  TAC  AAG  GAC  TTT  CTC  TGG  TTT  TTC  TCC  AAG  AGA         2725
Leu  Tyr  Tyr  Tyr  Ala  Tyr  Lys  Asp  Phe  Leu  Trp  Phe  Phe  Ser  Lys  Arg
          430                      435                      440

TTC  AAA  TCT  GCT  GCC  ATG  TTA  GCT  GTC  TTT  GCT  GTA  TCT  GCT  GTA  GTA         2773
Phe  Lys  Ser  Ala  Ala  Met  Leu  Ala  Val  Phe  Ala  Val  Ser  Ala  Val  Val
     445                      450                      455

CAC  GAA  TAT  GCC  TTG  GCT  GTT  TGC  TTG  AGC  TTT  TTC  TAT  CCC  GTG  CTG         2821
His  Glu  Tyr  Ala  Leu  Ala  Val  Cys  Leu  Ser  Phe  Phe  Tyr  Pro  Val  Leu
460                      465                      470                      475

TTC  GTG  CTC  TTC  ATG  TTC  TTT  GGA  ATG  GCT  TTC  AAC  TTC  ATT  GTC  AAT         2869
Phe  Val  Leu  Phe  Met  Phe  Phe  Gly  Met  Ala  Phe  Asn  Phe  Ile  Val  Asn
                    480                      485                      490

GAT  AGT  CGG  AAA  AAG  CCG  ATT  TGG  AAT  GTT  CTG  ATG  TGG  ACT  TCT  CTT         2917
Asp  Ser  Arg  Lys  Lys  Pro  Ile  Trp  Asn  Val  Leu  Met  Trp  Thr  Ser  Leu
               495                      500                      505

TTC  TTG  GGC  AAT  GGA  GTC  TTA  CTC  TGC  TTT  TAT  TCT  CAA  GAA  TGG  TAT         2965
Phe  Leu  Gly  Asn  Gly  Val  Leu  Leu  Cys  Phe  Tyr  Ser  Gln  Glu  Trp  Tyr
               510                      515                      520

GCA  CGT  CGG  CAC  TGT  CCT  CTG  AAA  AAT  CCC  ACA  TTT  TTG  GAT  TAT  GTC         3013
Ala  Arg  Arg  His  Cys  Pro  Leu  Lys  Asn  Pro  Thr  Phe  Leu  Asp  Tyr  Val
          525                      530                      535

CGG  CCA  CGT  TCC  TGG  ACT  TGT  CGT  TAC  GTG  TTT  TAGAAGCTTG  GACTTTGTTT           3066
Arg  Pro  Arg  Ser  Trp  Thr  Cys  Arg  Tyr  Val  Phe
540                      545                      550

CCTCCTTGTC  ACTGAAGATT  GGGTAGCTCC  CTGATTTGGA  GCCAGCTGTT  TCCAGTTGTT               3126

ACTGAAGTTA  TCTGTGTTAT  TTGGACCACT  CCAGGCTTTA  CAGATGACTC  ACTCCATTCC               3186

TAGGTCACTT  GAAGCCAAAC  TGTTGGAAGT  TCACTGGAGT  CTTGTACACT  TAAGCAGAGC               3246

AGAACTTTTT  TTGTGGGGCT  GGGTGGGGGG  AGAAGACCGA  CTAACAGCTG  AAGTAATGAC               3306

AGATTGTTGC  TGGGTCATAT  CAGCTTTATC  CCTTGGTAAT  TATATCTGTT  TTGTTTCTTG               3366

ACTCTGTCCA  ATCAGAGAAT  AAACATCATA  GTTCTTGGC   CACTGAATTA  GCCAAAACAC               3426

TTAGGAAGAA  ATCACTTAAA  TACCTCTGGC  TTAGAAATTT  TTTCATGCAC  ACTGTTGGAA               3486

TGTATGCTAA  TTGAACATGC  AATTGGGGAA  GAAAAAATGT  AGAATGATTT  TGCTATTTC                3546

TAGTAGAAAG  AAAATGTCTG  TTTTCCAAAG  ATAATGTTAT  ACATCCTATT  TTGTAATTTT               3606
```

-continued

```
TTTGAAAAAA GTTCAATGTT CAGTTTTCCT TAGTTTTTAC CTTGTTTTCT CTATAGGTCA      3666

TGATTTCTGT GAAGCAAAAA GATGCCTTTT ACCATGAATT CTTGAGTTTA CATCAATAAT      3726

ATTGTATATT AAGGGGATCA GAAGTAGGAA GGAAAAAATA AGAGATAGCA GAGGAAAAAG      3786

AAAAACATTT CCTCTTATAA CTTCTGAAGT AATTTGTAAA AAAGATTTGT AGAGTCAATC      3846

ATGTGTTTAA ATTATTTTAT CACAAACTTA ACATGGAAGA TATTCCTTTT TAACTTTGTG      3906

GTAACTTCTT TGAAGTTATT TAGAAATATC CTTTGGAACA ATTATTTTAT TGTCTAATAA      3966

ATATTGACTT CTCTTGAATT ATTTTGCAGA CTAGTGAGTC TGTAC                      4011
```

( 2 ) INFORMATION FOR SEQ ID NO:4:

( i ) SEQUENCE CHARACTERISTICS:
        ( A ) LENGTH: 550 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Val Gly Glu Glu Lys Met Ser Leu Arg Asn Arg Leu Ser Lys Ser
 1               5                  10                  15

Arg Glu Asn Pro Glu Glu Asp Glu Asp Gln Arg Asn Pro Ala Lys Glu
                20                  25                  30

Ser Leu Glu Thr Pro Ser Asn Gly Arg Ile Asp Ile Lys Gln Leu Ile
            35                  40                  45

Ala Lys Ile Lys Leu Thr Ala Glu Ala Glu Glu Leu Lys Pro Phe
        50                  55                  60

Phe Met Lys Glu Val Gly Ser His Phe Asp Asp Phe Val Thr Asn Leu
 65                  70                  75                  80

Ile Glu Lys Ser Ala Ser Leu Asp Asn Gly Gly Cys Ala Leu Thr Thr
                85                  90                  95

Phe Ser Val Leu Glu Gly Glu Lys Asn Asn His Arg Ala Lys Asp Leu
            100                 105                 110

Arg Ala Pro Pro Glu Gln Gly Lys Ile Phe Ile Ala Arg Arg Ser Leu
        115                 120                 125

Leu Asp Glu Leu Leu Glu Val Asp His Ile Arg Thr Ile Tyr His Met
130                 135                 140

Phe Ile Ala Leu Leu Ile Leu Phe Ile Leu Ser Thr Leu Val Val Asp
145                 150                 155                 160

Tyr Ile Asp Glu Gly Arg Leu Val Leu Glu Phe Ser Leu Leu Ser Tyr
                165                 170                 175

Ala Phe Gly Lys Phe Pro Thr Val Val Trp Thr Trp Trp Ile Met Phe
            180                 185                 190

Leu Ser Thr Phe Ser Val Pro Tyr Phe Leu Phe Gln His Trp Arg Thr
        195                 200                 205

Gly Tyr Ser Lys Ser Ser His Pro Leu Ile Arg Ser Leu Phe His Gly
    210                 215                 220

Phe Leu Phe Met Ile Phe Gln Ile Gly Val Leu Gly Phe Gly Pro Thr
225                 230                 235                 240

Tyr Val Val Leu Ala Tyr Thr Leu Pro Pro Ala Ser Arg Phe Ile Ile
                245                 250                 255

Ile Phe Glu Gln Ile Arg Phe Val Met Lys Ala His Ser Phe Val Arg
            260                 265                 270

Glu Asn Val Pro Arg Val Leu Asn Ser Ala Lys Glu Lys Ser Ser Thr
        275                 280                 285
```

| Val | Pro | Ile | Pro | Thr | Val | Asn | Gln | Tyr | Leu | Tyr | Phe | Leu | Phe | Ala | Pro |
| 290 | | | | | 295 | | | | | 300 | | | | | |

| Thr | Leu | Ile | Tyr | Arg | Asp | Ser | Tyr | Pro | Arg | Asn | Pro | Thr | Val | Arg | Trp |
| 305 | | | | | 310 | | | | | 315 | | | | | 320 |

| Gly | Tyr | Val | Ala | Met | Lys | Phe | Ala | Gln | Val | Phe | Gly | Cys | Phe | Phe | Tyr |
| | | | | 325 | | | | | 330 | | | | | 335 | |

| Val | Tyr | Tyr | Ile | Phe | Glu | Arg | Leu | Cys | Ala | Pro | Leu | Phe | Arg | Asn | Ile |
| | | | 340 | | | | | 345 | | | | | 350 | | |

| Lys | Gln | Glu | Pro | Phe | Ser | Ala | Arg | Val | Leu | Val | Leu | Cys | Val | Phe | Asn |
| | | 355 | | | | | 360 | | | | | 365 | | | |

| Ser | Ile | Leu | Pro | Gly | Val | Leu | Ile | Leu | Phe | Leu | Thr | Phe | Phe | Ala | Phe |
| | 370 | | | | | 375 | | | | | 380 | | | | |

| Leu | His | Cys | Trp | Leu | Asn | Ala | Phe | Ala | Glu | Met | Leu | Arg | Phe | Gly | Asp |
| 385 | | | | | 390 | | | | | 395 | | | | | 400 |

| Arg | Met | Phe | Tyr | Lys | Asp | Trp | Trp | Asn | Ser | Thr | Ser | Tyr | Ser | Asn | Tyr |
| | | | | 405 | | | | | 410 | | | | | 415 | |

| Tyr | Arg | Thr | Trp | Asn | Val | Val | Val | His | Asp | Trp | Leu | Tyr | Tyr | Tyr | Ala |
| | | | 420 | | | | | 425 | | | | | 430 | | |

| Tyr | Lys | Asp | Phe | Leu | Trp | Phe | Phe | Ser | Lys | Arg | Phe | Lys | Ser | Ala | Ala |
| | | 435 | | | | | 440 | | | | | 445 | | | |

| Met | Leu | Ala | Val | Phe | Ala | Val | Ser | Ala | Val | Val | His | Glu | Tyr | Ala | Leu |
| | 450 | | | | | 455 | | | | | 460 | | | | |

| Ala | Val | Cys | Leu | Ser | Phe | Phe | Tyr | Pro | Val | Leu | Phe | Val | Leu | Phe | Met |
| 465 | | | | | 470 | | | | | 475 | | | | | 480 |

| Phe | Phe | Gly | Met | Ala | Phe | Asn | Phe | Ile | Val | Asn | Asp | Ser | Arg | Lys | Lys |
| | | | | 485 | | | | | 490 | | | | | 495 | |

| Pro | Ile | Trp | Asn | Val | Leu | Met | Trp | Thr | Ser | Leu | Phe | Leu | Gly | Asn | Gly |
| | | | 500 | | | | | 505 | | | | | 510 | | |

| Val | Leu | Leu | Cys | Phe | Tyr | Ser | Gln | Glu | Trp | Tyr | Ala | Arg | Arg | His | Cys |
| | | 515 | | | | | 520 | | | | | 525 | | | |

| Pro | Leu | Lys | Asn | Pro | Thr | Phe | Leu | Asp | Tyr | Val | Arg | Pro | Arg | Ser | Trp |
| | 530 | | | | | 535 | | | | | 540 | | | | |

| Thr | Cys | Arg | Tyr | Val | Phe |
| 545 | | | | | 550 |

( 2 ) INFORMATION FOR SEQ ID NO:5:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:5:

| Thr | Asn | Leu | Ile | Glu | Lys | Ser | Ala | Ser | Leu | Asp | Asn | Gly | Gly | Cys | Ala |
| 1 | | | | 5 | | | | | 10 | | | | | 15 | |

| Leu | Thr | Thr |

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide (v) FRAGMENT TYPE: internal (xi) SEQUENCE DESCRIPTION: SEQ ID NO:6:

Gly Arg Leu Val Leu Glu Phe Ser Leu Leu Ser Tyr Ala Phe
1               5                       10

(2) INFORMATION FOR SEQ ID NO:7:

(i) SEQUENCE CHARACTERISTICS:
      (A) LENGTH: 6 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:7:

Gly Phe Gly Pro Thr Tyr
1               5

(2) INFORMATION FOR SEQ ID NO:8:

(i) SEQUENCE CHARACTERISTICS:
      (A) LENGTH: 14 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:8:

Gly Tyr Val Ala Met Lys Phe Ala Gln Val Phe Gly Cys Phe
1               5                       10

(2) INFORMATION FOR SEQ ID NO:9:

(i) SEQUENCE CHARACTERISTICS:
      (A) LENGTH: 17 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:9:

Ala Arg Val Leu Val Leu Cys Val Phe Asn Ser Ile Leu Pro Gly Val
1               5                       10                      15

Leu